United States Patent [19]

Ratcliffe et al.

[11] Patent Number: 5,296,594

[45] Date of Patent: Mar. 22, 1994

[54] SIALIC ACID GLYCOSIDES, ANTIGENS, IMMUNOADSORBENTS, AND METHODS FOR THEIR PREPARATION

[75] Inventors: Robert M. Ratcliffe; Andre P. Venot; S. Zaheer Abbas, all of Edmonton, Canada

[73] Assignee: Alberta Research Council, Edmonton, Canada

[21] Appl. No.: 545,999

[22] Filed: Jun. 28, 1990

Related U.S. Application Data

[62] Division of Ser. No. 127,905, Dec. 2, 1987, Pat. No. 5,079,353.

[51] Int. Cl.$^5$ .................... C07H 5/06; C07K 3/20; G01N 33/531
[52] U.S. Cl. .................... 536/53; 435/7.23; 435/7.9; 435/188; 436/543; 436/544; 530/403; 530/413; 536/18.2
[58] Field of Search .............. 435/7.23, 7.9, 188; 436/544, 545, 546, 813, 543; 530/403, 413, 807; 536/53, 18.2

[56] References Cited

U.S. PATENT DOCUMENTS

| 4,172,124 | 10/1979 | Koprowski et al. | 424/85.8 |
|---|---|---|---|
| 4,471,057 | 9/1984 | Koprowski et al. | 424/1.1 |
| 4,736,022 | 4/1988 | Rademacher et al. | 536/22 |
| 4,761,401 | 8/1988 | Couchman et al. | 514/53 |
| 4,767,845 | 8/1988 | Lemieux et al. | 536/18.2 |
| 4,774,231 | 9/1988 | Petitou et al. | 514/53 |
| 4,794,176 | 12/1988 | Lemieux et al. | 536/53 |
| 4,794,179 | 12/1988 | Lemieux et al. | 536/53 |
| 4,801,583 | 1/1989 | Petitou et al. | 514/54 |
| 4,818,816 | 4/1989 | Petitou et al. | 536/55.2 |
| 4,904,596 | 2/1990 | Hakomori | 435/240.27 |
| 4,980,462 | 12/1990 | Karlsson et al. | 436/53 |
| 5,035,516 | 7/1991 | Roy et al. | 536/4.1 |
| 5,075,218 | 12/1991 | Jette et al. | 435/7.23 |

FOREIGN PATENT DOCUMENTS

| 0069678 | 1/1983 | European Pat. Off. . |
|---|---|---|
| 0146090 | 6/1985 | European Pat. Off. . |
| 0165811 | 12/1985 | European Pat. Off. . |
| 0166442 | 1/1986 | European Pat. Off. . |
| 0173663 | 3/1986 | European Pat. Off. . |
| 0204344 | 12/1986 | European Pat. Off. . |
| 0242736 | 10/1987 | European Pat. Off. . |
| 0255717 | 2/1988 | European Pat. Off. . |
| 0256485 | 2/1988 | European Pat. Off. . |
| 0273388 | 7/1988 | European Pat. Off. . |
| 01080603 | 11/1982 | Japan . |
| 0155201 | 7/1985 | Japan . |
| WO 84/00758 | 3/1984 | PCT Int'l Appl. . |
| WO 89/09275 | 10/1989 | PCT Int'l Appl. . |

OTHER PUBLICATIONS

Paulsen, et al., *Chem. Abst.*, 105: Abst. No. 24548x (1986).
Hannson, et al., *J. Biol. Chem.*, 260:9388–9392 (1985).
Johnson, et al., *Proc. IXth International Symposium of Glycoconjugates*, Lille, France E107 (1987).
Hanish, et al., *Chem,. Abst.* 102(3): Abst No. 22471F (1985).
Hanish, et al., *Eur. J. Biochem.*, 144:467–473 (1984).
Fukushima, et al., *Chem. Abst.* 102(13): abst. No. 11029 k (1985).
Fukushima, et al., *Cancer Res.* 44:5279–5285 (1985).
Lamblin et al., *J. Biol. Chem.* (1984) 259 (14):9501–9058.
Kiyoyasu et al., *Chem. Abstracts* (1985) 102(13):507.

(List continued on next page.)

*Primary Examiner*—David Saunders
*Attorney, Agent, or Firm*—Burns, Doane, Swecker & Mathis

[57] ABSTRACT

The stereochemistry of sialylation of an acceptor saccharide to obtain an α (2-3) or α (2-6) linkage is controlled to favor the a anomer by use of an aromatic ester of the sialyl reagent. The resulting intermediate α (2-3) and α (2-6) sialylated intermediate disaccharide blocks are useful in the synthesis of antigenic substances which can be used to raise antibodies useful in diagnosis and therapy, and can themselves be used as reagents in various applications. The preparation of the tetrasaccharide antigens corresponding to the 19-9 and sialyl-X antigens characteristic of malignant tissue illustrates the application of this method.

8 Claims, 17 Drawing Sheets

OTHER PUBLICATIONS

Magnani et al., *J. Biol. Chem.* (1982) 257(23):14365–14369.
Hanisch et al., *Chem,. Abstracts* (1985) 102(3):511–512.
Derappe et al., *Carbohydrate Res.* (1986) 145:341–347.
Fukuda et al., *J. Biol. Chem.* (1984) 259(8):4781–4791.
Parkkinen et al, *Chem. Abstracts* (1984) 100(25):218.
Achiba et al., *Chem. Abstracts* (1988) 108(19):694.
Numata et al., *Carbohydrate Res.* (1987) 163:209–225.
Tamura et al., *Carbohydrate Res.* (1990) 207:153–165.
Ogura et al., *Carbohydrate Res.* (1987) 167:77–86.
Roy et al., *J. Carbohydrate Chem.* (1987) 6(1):161–165.
Schauer *Adv. Carbohydrate Chem. Biochem.* (1982) 40:131–234.
Corifield et al., "Salic Acids, Chemistry, Metabolism and Function,", pp. 5–50, Shauer, R. ed., Springer-Verlag, New York (1982).
Hakomori *TIBS* (Oct. 1984) pp. 453–459.
Feizi et al., *TIBS* (Jan. 1985) pp. 24–29.
Sabesan et al., *J. Amer. Chem. Soc.* (1986) 108:2068–2080.
Paulsen et al., *Carbohydrate Res.* (1984) 125:47–64.
Paulsen et al., *Carbohydrate Res.* (1985) 144:205–229.
Ogawa et al., *Tetrahedron Letters* (1986) 27(47):5739–5742.
Pozgay et al., *J. Carbohydrate Chem.* (1987) 6(1):41–55.
Paulsen et al., *Carbohydrate Res.* (1985) 137:63≧77.
Paulson et al., *Pure & Appl. Chem.* (1984) 56(7):797–805.
Loomes et al., *Nature* (2984) 307:560–563.
Holmes, et al., "Biosynthesis of the Sailyl–Le$^x$ Determinant Carried by Type 2 Chain Glycosphingo–lipids (IV$^3$ Neu AC lll$^3$ VI$^3$ III $^3$V$^3$ Fuc$_2$ in Lc$_6$) in Human Lung Carcinoma PC9 Cells", *J. Biol. Chem.*, 261:3737–3743 (1986).
Howard, et al., "The GDP–fucose: A–Acetylglucosaminide 3–αL–Fucosytransferases of LEC11 and LEC12 Chinese Hamster Ovary Mutants Exhibit Novel Specificities for Glycolipid Substrates", *J. Biol. Chem.*, 262: 16,8340–16,837 (1987).
Johnson, et al., "Sialyl Compounds as Acceptor Substrates for Fucosyltransferases in Normal and Leukaemic Human Granulocytes", *Biochem. Soc. Trans.*, 15:396 (1987).

SIALIC ACID GLYCOSIDES, ANTIGENS, IMMUNOADSORBENTS, AND METHODS FOR THEIR PREPARATION

This application is a division, of application Ser. No. 07/127,905 filed, Dec. 2, 1987 now U.S. Pat. No. 5,079,353.

TECHNICAL FIELD

The invention relates to the fields of oligosaccharide synthesis and antigen/antibody interaction. Specifically, the invention concerns synthesis of oligosaccharide haptens. These haptens can be used as antigens which are rendered immunogenic by conjugation to raise antibodies useful in diagnosis and therapy. The synthetic haptens can also be used in immunosorbents for preparation, isolation, removal and purification of the corresponding antibodies, and are useful in assay reagents.

BACKGROUND OF THE INVENTION

The following references are cited in this Background Section:
1. Schauer, R., *Adv Carbohydr Chem Biochem* (1982) 40: 131 to 234.
2. Corfield, A. P., et al, "Sialic Acids, Chemistry, Metabolism and Function", pp 5-50, Schauer, R., ed., Springer-Verlag, New York (1982).
3. Hakomori, S., *TIBS* (1984) 453 to 459.
4. Feizi, T., et al, *TIBS* (1985) 24 to 29.
5. Paulsen, H., et al, *Carbohydr Res* (1986) 146: 147 to 153.
6. Sabesan, S., et al, *J Amer Chem Soc* (1986) 108: 2068 to 2080.
7. Paulsen, H., et al, *Carbohydr Res* (1984) 125: 47 to 64.
8. Paulsen, H., et al, *Carbohydr Res* (1985) 144: 205 to 229.
9. Ogawa, T., et al, Eur Pat Appl Pub No 146090, Jun. 26, 1985.
10. Ogawa, T., et al, *Tetrahedron Lett* (1986) 27:5739 to 5742.
11. Pozsgay, V., et al, *Carbohydr Chem* (1987) 6: 41 to 55.
12. Paulsen, H., et al, *Carbohydr Res* (1985) 137: 63 to 77.
13. Ogawa, T., et al, Eur Pat Appl Pub No. 166442, Jan. 2, 1986.
14. Paulson, J. C., et al, *Pure Appl Chem* (1984) 56: 797-806.
15. Loomes, L. M., et al, *Nature* (1984) 307: 560-563.

Sialic acid glycosides are known to occur in a wide variety of biological materials [1,2] in the form of gangliosides and complex oligosaccharides attached to proteins. These are present in bodily fluids and on cell surfaces. Sialic acid-containing structures have been shown to be important for the attachment of viral particles to tissues and protection of proteins from proteolysis. They are known to be higher in concentration [3,4] in sera of cancer patients as opposed to normal individuals; they also occur on the tissues of cancer patients. Specifically structures having as terminal tetrasaccharides 19-9 and sialo-X moieties are related to the cancerous state. Assays taking advantage of this association are described in U.S. Pat. No. 4,471,057; and antibody production to tumors bearing these haptens in U.S. Pat. No. 4,172,124.

In order to detect, quantify and study the tetrasaccharides (and their precursors and biosynthesis) it is advantageous to obtain them and their antibodies in practical amounts. The availability of these moieties from nature through isolation is tedious and results in limited quantities of material that must be purified for further use. Also, material that is obtained through isolation does not provide for useful modified structures, such as synthetic antigens or immunoadsorbents.

An alternative to isolation of such interesting structures to provide well-defined materials for the study of biological actions is chemical synthesis. The chemical synthesis of sialosides in high anomeric purity and reasonable yields has remained a difficult challenge for chemists in the recent past [5,6].

There has been moderate success in chemically preparing sialosides with 2-6 linkages, however most reaction conditions with various substrates give anomeric mixtures ($\alpha/\beta$ equals near 1/1) [7,8,9,10]. A wide variety of reaction conditions has been reported, including variation of substrate alcohol, catalyst, and solvent. The result of these reactions is wide variation of overall yield of sialosides (10-80%) but generally consistent $\alpha/\beta$ ratios of near 1/1 with few exceptions [7,11]. Such mixtures are tedious and difficult to separate to obtain the desired alpha-sialoside.

The reported methods for forming a glycosidic linkage between the two position of sialic acid and the three position of galactosides (2-3 linkage) and derivatives of these, have been even less successful [5]. Overall yields of sialosides ($\alpha$ and $\beta$) are consistently lower and anomeric purity is poor. Again a wide variety of alcohols, catalysts and solvents have been used in these attempts. As it has been shown [7,12] that there is great variation obtained (both in anomeric specificity and overall yield) with various acceptors, donors and reaction conditions in the formation of 2-6 linkages, extrapolation from these results to the formation of 2-3 linkages in a meaningful way is difficult and uninstructive. The danger of such comparisons is well known to the skilled chemist.

All but five reported examples of sialoside synthesis of higher oligosaccharides use a step-wise synthetic strategy. The examples of "block synthesis" used to produce higher sialosides involving the use of a 2-6 block show limited versatility, or poor anomeric specificity [8,10,13].

The one reported example of the synthesis of a 2-3 block suffers from the same problems more severely. This block is produced through the reaction of a sialoside derivative with a 3,4 diol of a disaccharide which results in the 2-3 linkage in 17% yield with an $\alpha/\beta$ ratio of 0.4. This block has not been used for the synthesis of larger oligosaccharides to effect an intersugar linkage [13].

The one consistent factor in all strategies for the synthesis of higher sialosides is the use of a methyl ester as the temporary blocking group for the acid moiety of the sialosyl halide. Use of this group would seem sensible as it provides the necessary blocking while conferring minimal steric interference adjacent to the carbon through which the glycosidic linkage is to be formed, and it is believed that the inherent steric restriction around carbon two of ketoses is, in part, also responsible for the increased production of undesirable unsaturated products during glycosylation of sialic acid derivatives.

The use of a methyl ester derivative of the sialyl halogenose results in limitation of subsequent use of the product oligosaccharide for the formation of synthetic antigens and immunoadsorbents which are among the objects of this invention. This limitation is due to the desirability of being able to easily deblock a synthetic sialoside, including its acid group, while maintaining an ester group present in a linking arm, attached to the oligosaccharide, for subsequent activation to allow coupling of the sialoside to proteins and insoluble carriers. Such coupling is achieved for most oligosaccharides through attachment of a synthetic oligosaccharide to an amino or carboxylic acid group on a protein carrier. The strategies of coupling to carboxylic acid groups in proteins are precluded, as it would be commonplace to use an amino-terminated linking arm. This would result in undesirable self-polymerization of the now carboxylic unprotected synthetic oligosaccharide. Therefore, terminally derivatized acid linking arms which, by the nature of the ester or other derivative, can be chemically differentiated from the ester used to block the sialyl acid group are preferred, and these derivatives must be persistent through the total deblocking of the sialoside.

There are few reports in the prior art of the preparation of any synthetic sialyl oligosaccharide antigens and immunoadsorbents or the properties of these. There are no reports,to our knowledge, of higher (more than one or two different sugar residues) synthetic sialyl oligosaccharide antigens or immunoadsorbents.

DISCLOSURE OF THE INVENTION

The invention provides efficient synthesis of sialosides in high anomeric purity to allow the preparation of synthetic antigens and immunoadsorbents that are useful for the preparation, detection, purification or removal of antibodies, lectins, receptors or other biomolecules which have an affinity for such structures. The synthesis employs a synthetic block which contains the critical glycoside linkage and which can be converted to a variety of end products. The blocks are thus synthetic sialosides that are readily converted to the products and their useful corresponding antigens and immunoadsorbents. A particular advantage of the invention disclosed herein results from the use of esters other than methyl for blocking the carboxyl of the intermediate sialohalogenose, such as the benzyl or phenacyl esters. These intermediates give a higher yield of product, and, specifically, yield higher desired anomeric purity in obtaining the α-sialoside blocks.

As the synthetic blocks disclosed herein are of a minimum size (sialosyl disaccharide); they can be used to synthesize any of the naturally occurring α (2-3) or α (2-6) sialosides, or alternative forms containing these moieties. This approach also permits a wide range of linking arms, since the chemistry of the linking arm attached to the reducing end of the higher oligosaccharide does not significantly alter the attachment of the block to additional sugars.

The synthetic method of the invention can be applied specifically to the synthesis of certain sialyl-containing trisaccharides and to certain tetrasaccharides, especially to trisaccharide precursors and the tetrasaccharides designated 19-9 and sialo-X. The 19-9 and sialo-X tetrasaccharides which exemplify the synthetic methods of the invention are known to be associated with malignancy. Antibodies immunoreactive with these haptens are useful as diagnostic and potential therapeutic tools in the management of malignancy. The intermediate saccharides are also substrates to assay the relevant glycosyltransferases.

All the synthetic haptens of the invention can be used in the preparation of both antigens and immunosorbents. The immunosorbents are useful for the purification and detection of antibodies reactive with the haptens. The haptens, when attached to a solid support to form immunosorbents, can be used to remove or purify these antibodies from blood or plasma. In addition, the labeled haptens can also be used in diagnostic assays for substances containing the haptens or for their complementary antibodies.

Thus, in one aspect, the invention is directed to compounds containing moieties of the formula:

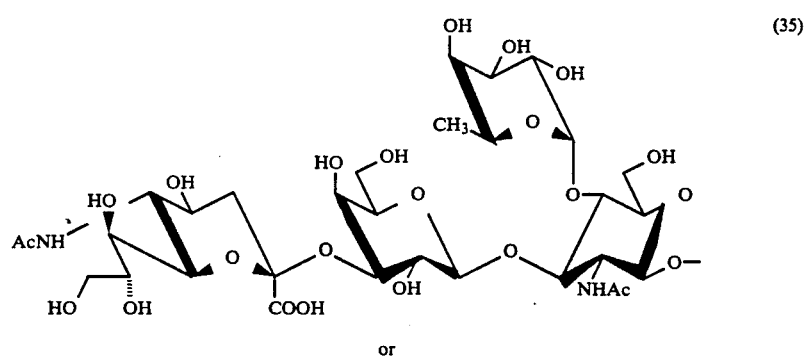

(35)

or

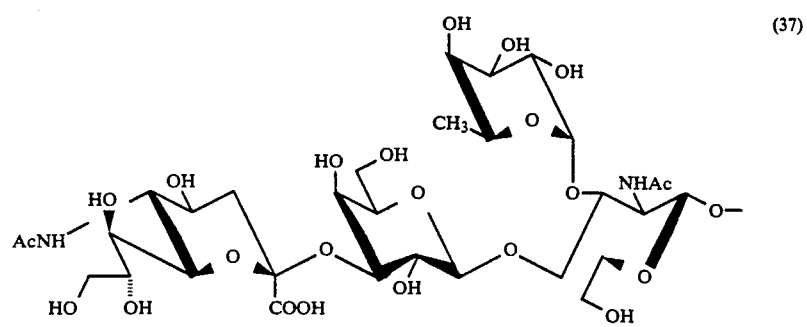

(37)

wherein Ac is acyl (Cl-6), representing sialo-Lewis$^a$ (19-9) and sialo-X, respectively. These moieties may be prepared in isolated forms per se, and further may be conjugated to solid support, to an antigen-forming carrier, to a label, to another sugar residue, or to a linking arm useful in effecting such conjugations. The intermediate trisaccharides are similarly useful; in addition, the trisaccharides can serve as substrates for the assay of samples for the relevant glycosyltransferase. The invention includes these trisaccharides and their derivatives.

In still another aspect, the invention is directed to a method to effect a high yield of the α anomeric 2-3 sialyl-galactopyranosyl linkage. This method comprises reacting a sialyl halide wherein the acid function is blocked as an aromatic ester with a suitably protected galactopyranosyl acceptor to give an additional synthetic block or useful end product.

In another aspect, the invention is directed to block intermediates useful in the synthesis of oligosaccharides containing an α (2-3) sialyl galactopyranoside unit. The invention is also directed to methods for producing desired oligosaccharides using this intermediate block, and to additional intermediates characteristic of this method. In still another aspect, the invention is directed to the formation of intermediate α (2-6) disaccharide blocks, and to the use of these blocks in further synthesis.

Thus, also included is a method to effect a high yield of the α anomeric (2-6) sialyl-galacto pyranosyl linkage, which method is analogous to that leading to the α anomer of the (2-3) linked product. A further aspect is directed to the resulting block intermediate and to methods for producing desired oligosaccharides using this 2-6 intermediate block and the associated intermediates involved in this further synthesis.

All of the foregoing intermediates may be characterized as "haptens" and are useful as described below.

In other aspects, the invention is directed to methods of using the tetra-and trisaccharide moieties or other haptens or their conjugates for diagnosis, isolation and purification procedures, and therapy.

In still other aspects, the invention is directed to methods of preparation of the haptens and of their conjugates, including the method comprising deprotecting the protected forms thereof.

Modes of Carrying Out the Invention

Figure 1:
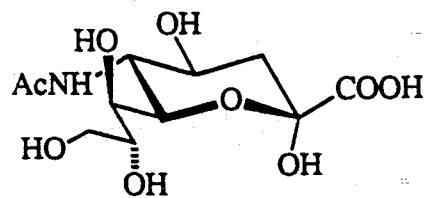
FIGS. 1 through 43 illustrate the structure of compounds 1 through 43 respectively.
Figure 2:
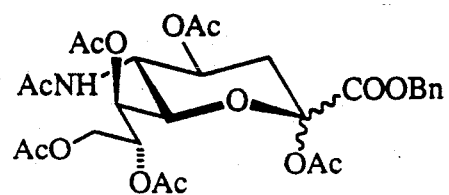
Figure 3:
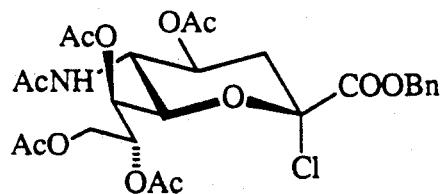
Figure 4:
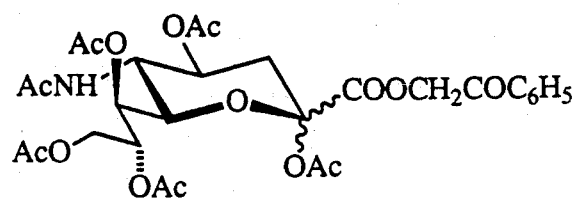
Figure 5:
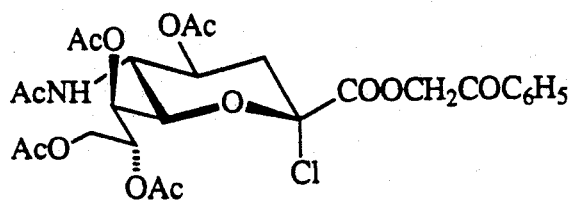
Figure 6:
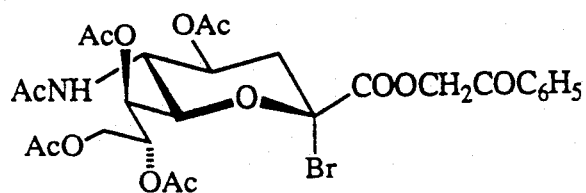
Figure 7:
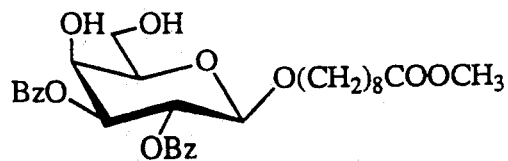
Figure 8:
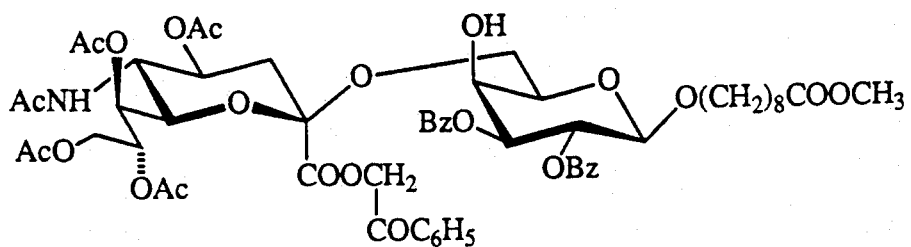
Figure 9:
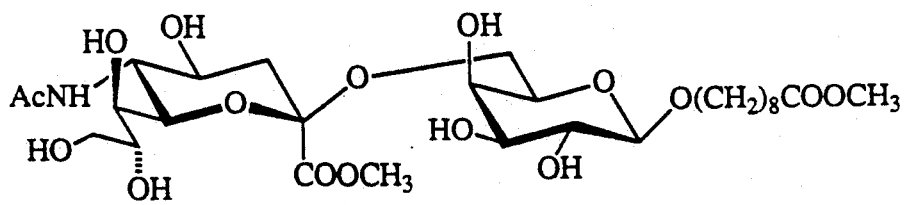
Figure 10:
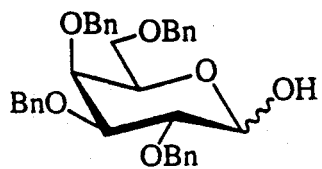
Figure 11:
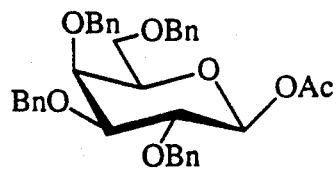
Figure 12:
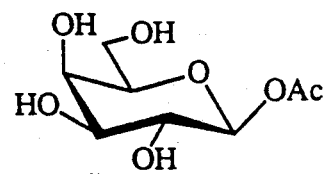
Figure 13:
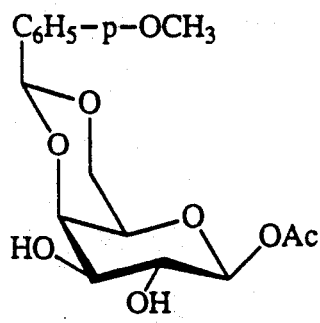
Figure 14:
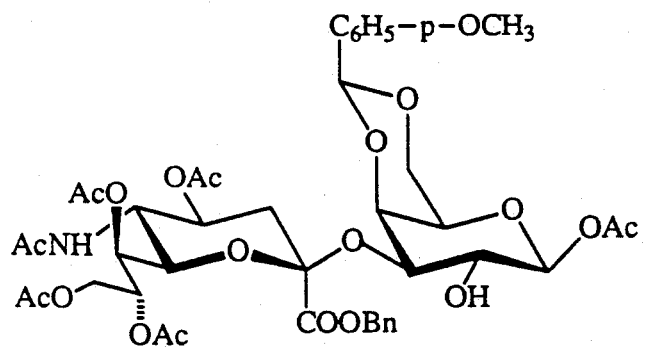
Figure 15:
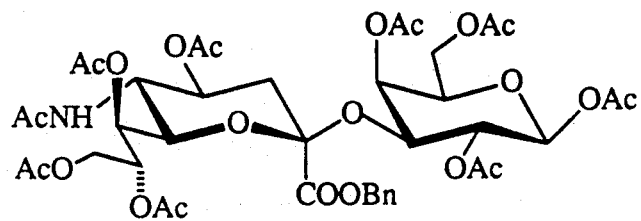
Figure 16:
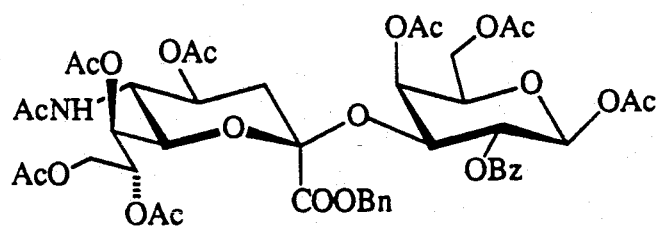
Figure 17:
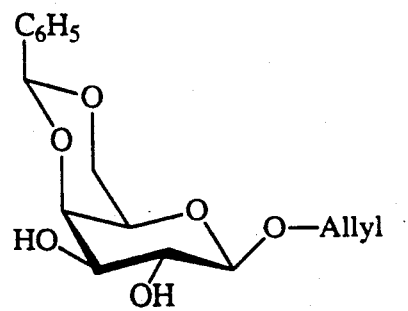
Figure 18:
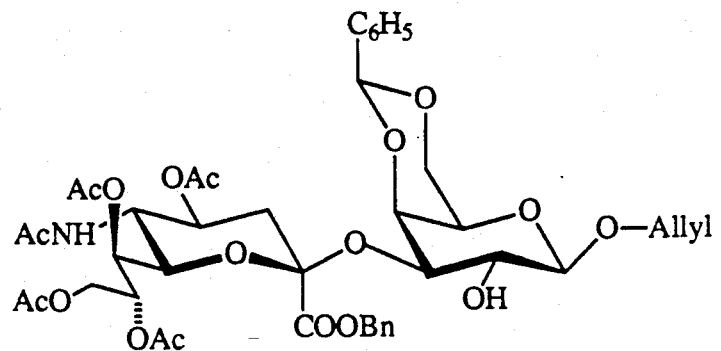
Figure 19:
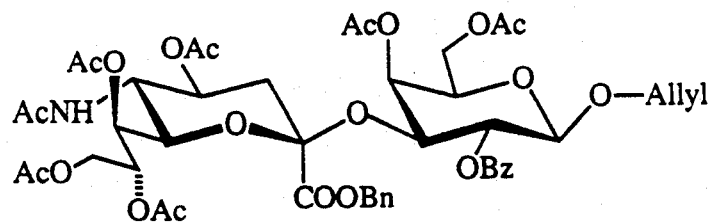
Figure 20:
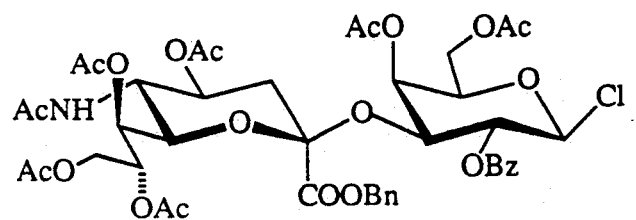
Figure 21:
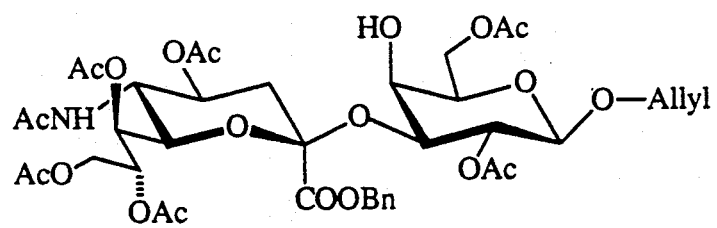
Figure 22:
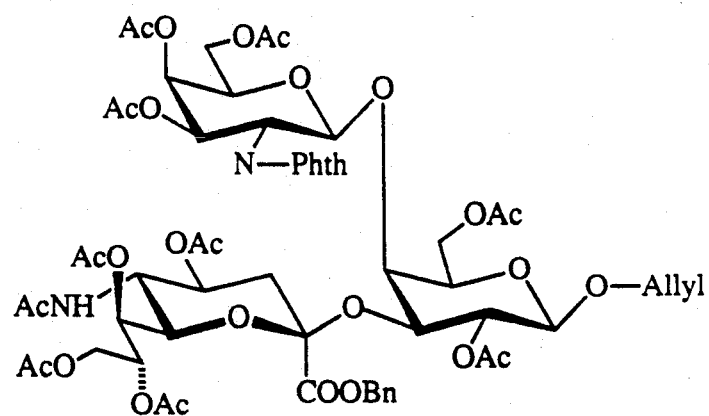
Figure 23:
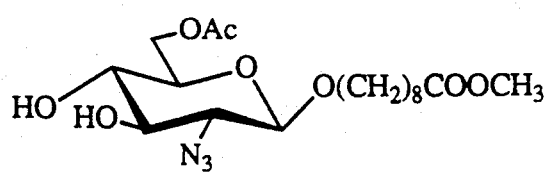
Figure 24:
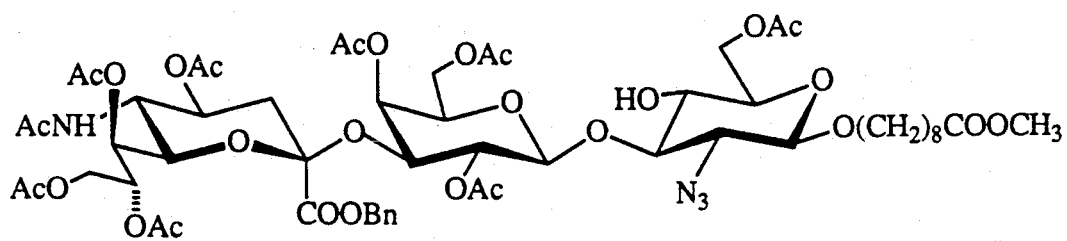
Figure 25:
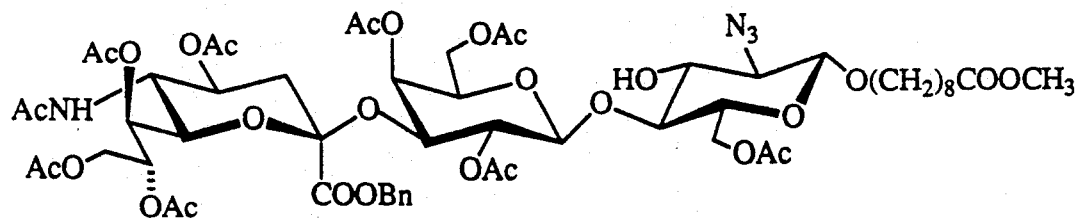
Figure 26:
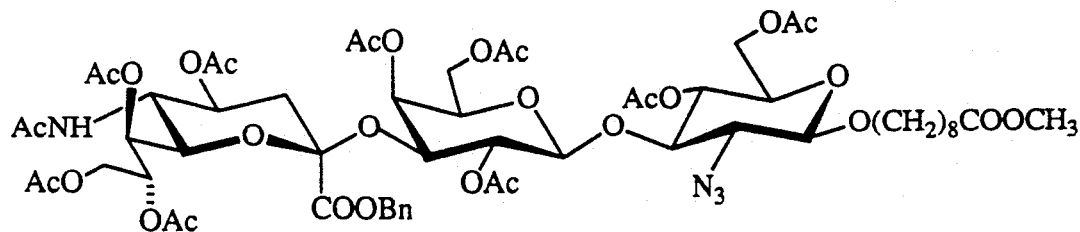
Figure 27:
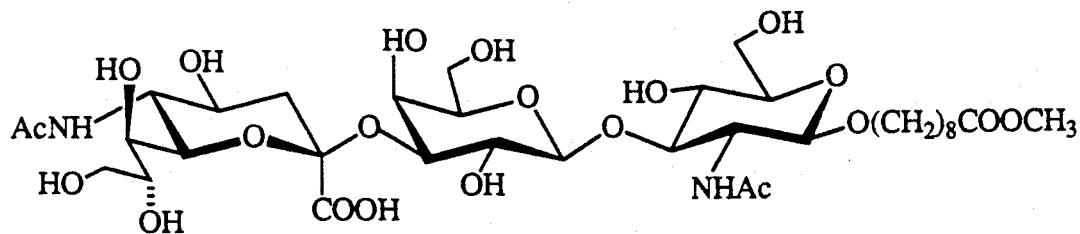
Figure 28:
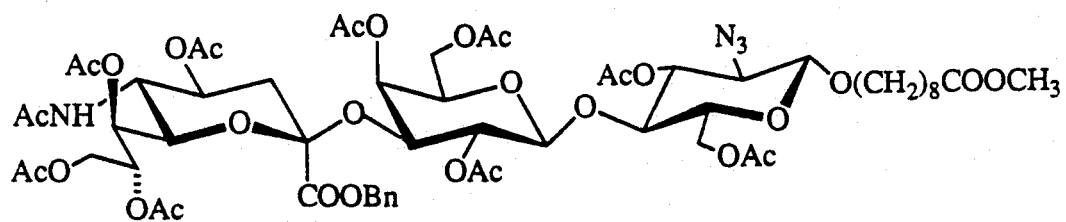
Figure 29:
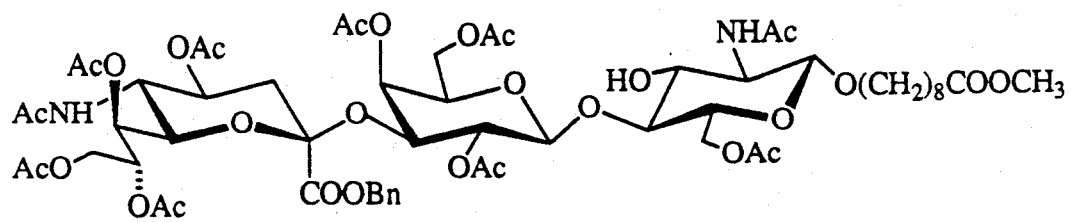
Figure 30:
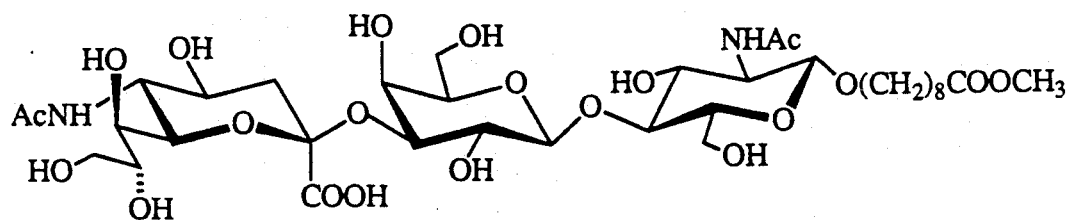
Figure 31:
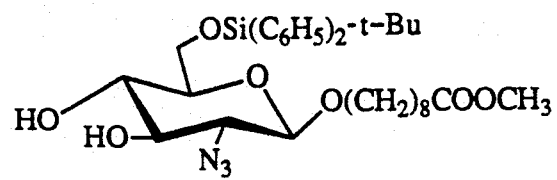
Figure 32:
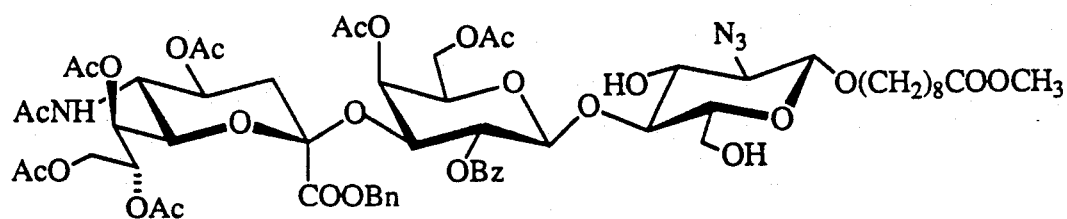
Figure 33:
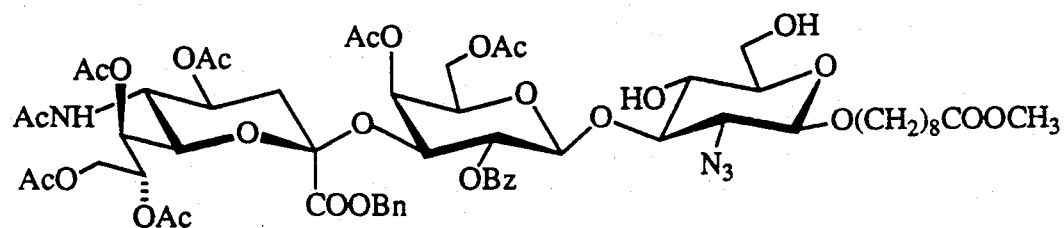
Figure 34:
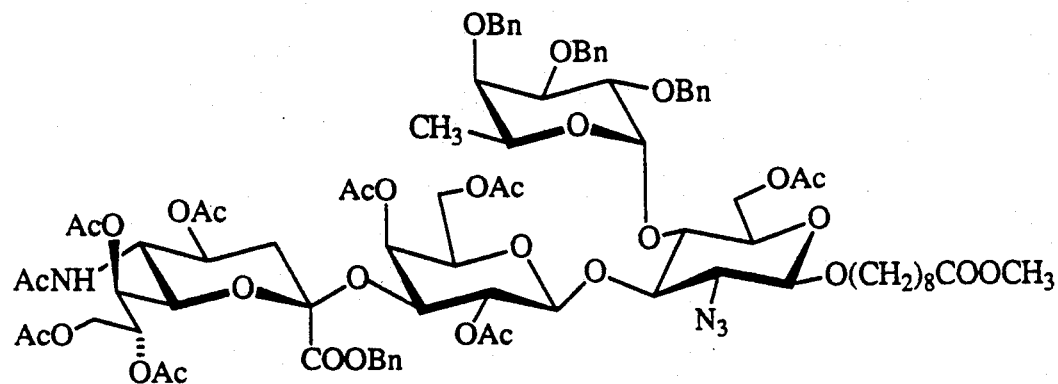
Figure 35:
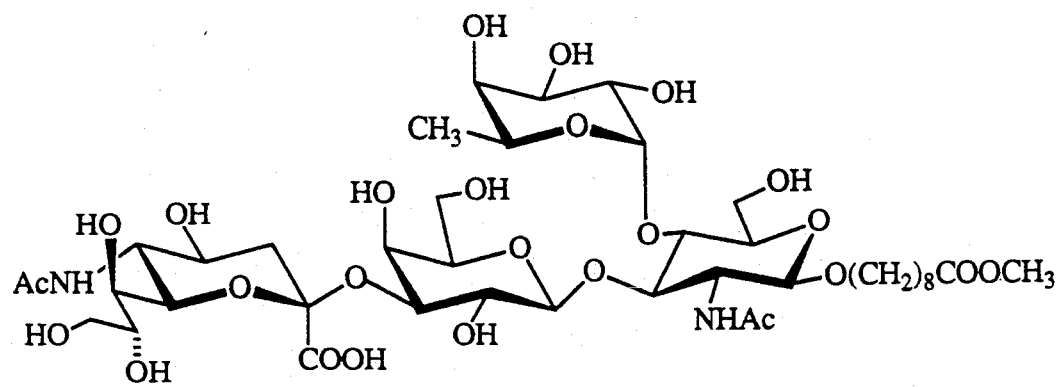
Figure 36:
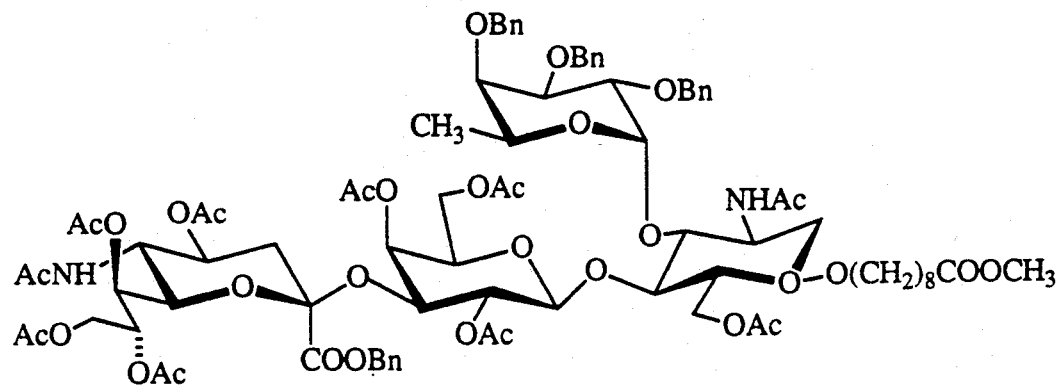
Figure 37:
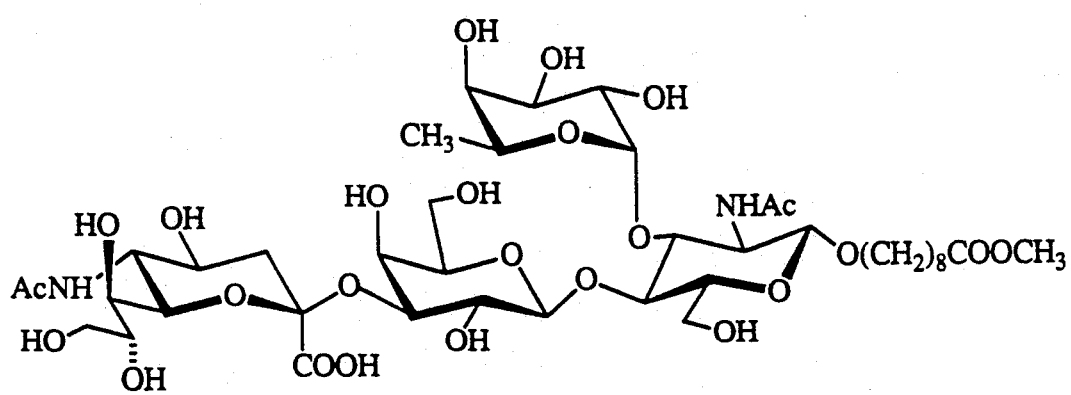
Figure 38:
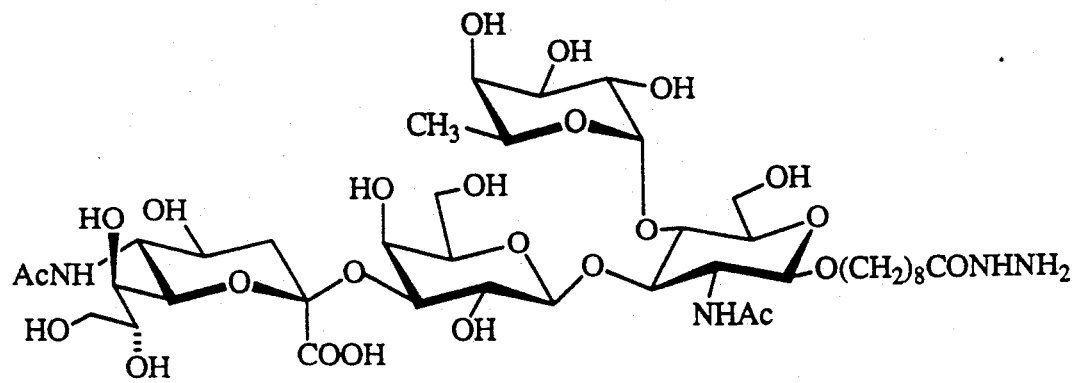
Figure 39:
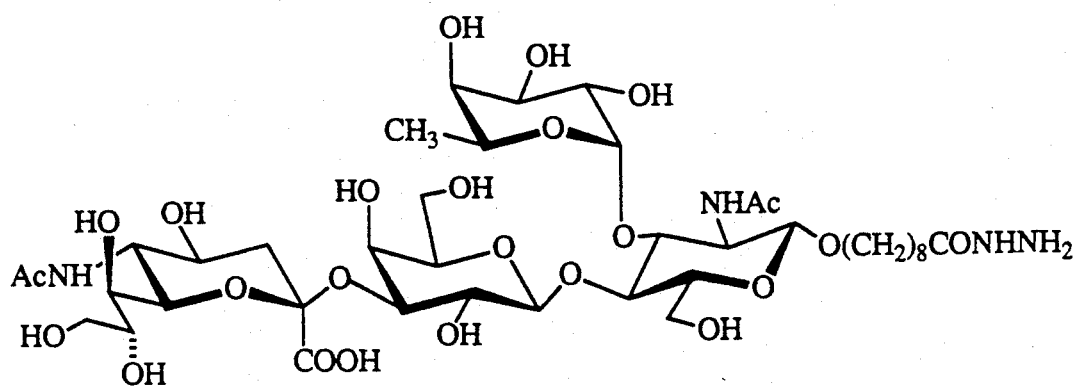
Figure 40:
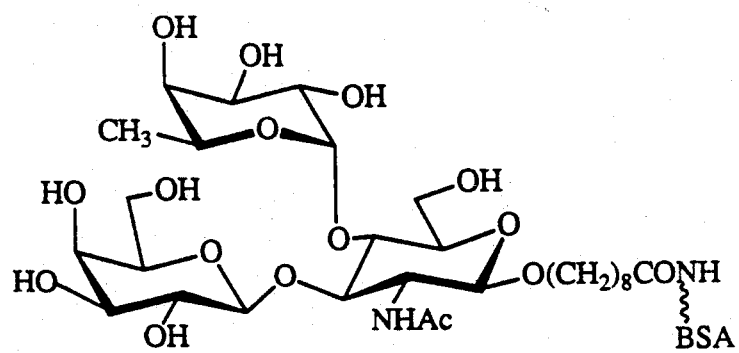
Figure 41:
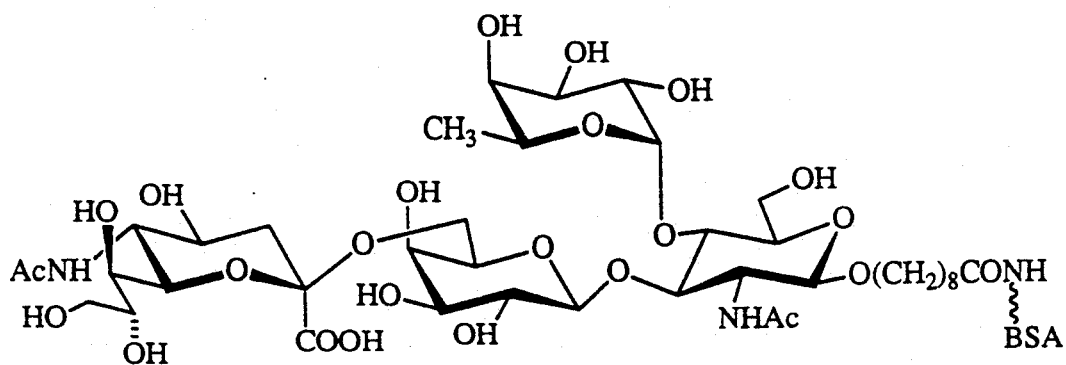
Figure 42:
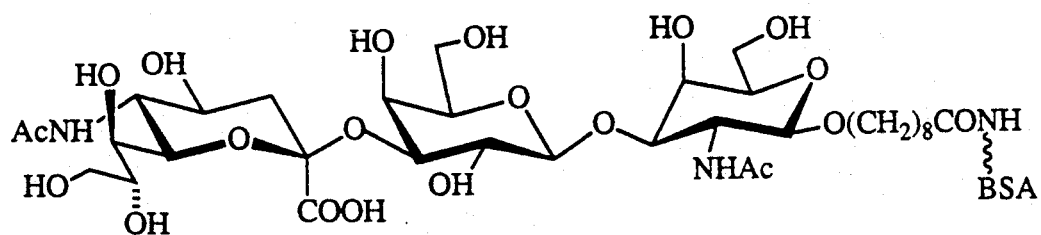
Figure 43:
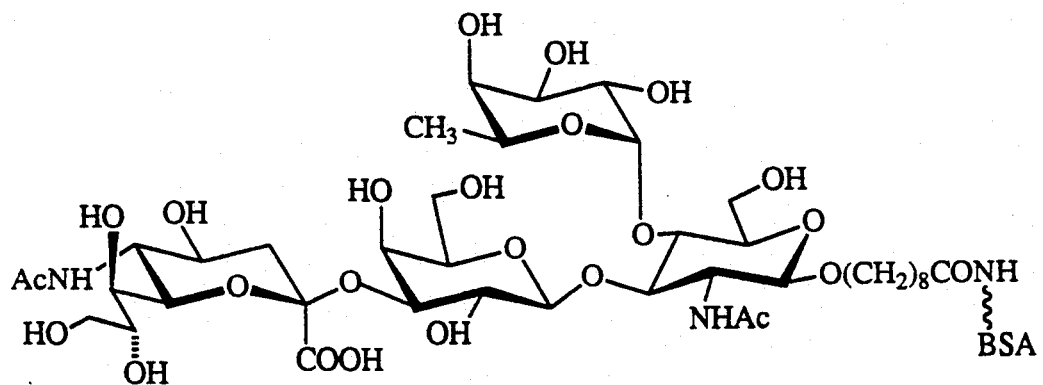

The invention provides as a convenient synthetic block, α (2-3) sialyl galactopyranoside, a disaccharide which occurs in a number of important oligosaccharides. This block is useful in synthesis of a number of oligosaccharides which are significant in various biological processes. The use of this intermediate block is illustrated in the preparation of two particular trisaccharides of the structures

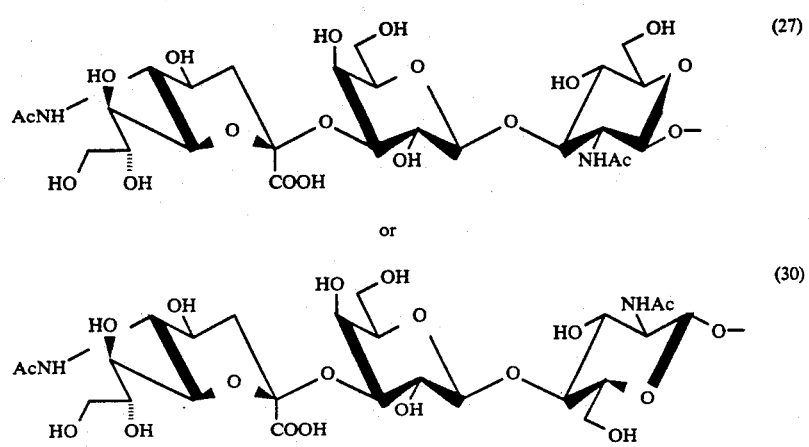

These trisaccharides can then be converted to the tetrasaccharides sialo-Lewis$^a$ (19-9) and sialo-X, the structures of which are shown above.

All of the 19-9 and sialo-X and their trisaccharide intermediates contain an α (2-3) sialyl-galactopyranosyl unit. This unit is linked β (1-3) or β (1-4) to N-acetyl glucosamine to give the trisaccharidic precursors for the 19-9 and sialo-X tetrasaccharides, respectively. Further attachment of α-fucose (1-4) or (1-3) to these trisaccharides provide for the 19-9 and sialo-X, respectively.

The tri-and tetrasaccharides are produced in a manner which permits them to be easily converted into synthetic immunoadsorbents and antigens that are useful for the preparation, isolation, detection and purification of the corresponding antibodies. The (2-3) sialo-containing block can also be used in moieties which can detect lectins or receptors, such as bacterial and viral receptors, that serve as adhesins[14,15].

The tetrasaccharide moieties illustrated are known to be associated with malignant tissue. They can be prepared, as illustrated, already conjugated to convenient linkers as shown in compounds 35 and 37 herein, to permit convenient attachment to chromatographic supports or to antigen forming carriers, or to labels.

In an analogous manner, a sialo disaccharide block having an α (2-6) glycosidic linkage is provided for subsequent conversions to higher saccharide moieties having utilities similar to those described above for the sialo α(2-3) block derived saccharides.

A. Definitions and Scope

As used herein, "protecting group" refers to moieties ordinarily used in oligosaccharide synthesis to prevent reaction of the hydroxyl groups in the reactions being conducted. Suitable protecting groups include acyl groups, especially lower acyl such as propionyl and acetyl, aromatic acyl groups, such as benzoyl, silyl groups such as trialkyl-or alkylarylsilyl, in particular t-butyldiphenylsilyl, and acetal derivatives, all protecting for hydroxy moieties, and protecting groups for carboxylic moieties such as phenyl and benzyl. Any commonly used protecting group known in the art for use in oligosaccharide synthesis is included.

The saccharide haptens of the invention are shown in structures containing their essential features, and wherein the hemiacetal is of the form —OY rather than —OH. This convention is used because the saccharide hapten may be derivatized in various ways. Thus, Y may be simply H or alkyl (C1-6). Y may also be an additional sugar or saccharide, if the hapten is part of a larger carbohydrate. Y may be a linking arm useful to conjugate the hapten to solid supports or to other substances. Y may be or may include an immunogenicity-conferring substance, such as a protein or other "antigen-forming carrier" if the hapten is to be used as an antigen. Y may be or include a chromatographic support if the hapten is to be used as an immunoadsorbent. Y may include a label if the compound is to be used in assays. Where Y includes a solid support, carrier or label, conjugation of the hapten to same can be through a linking arm, and embodiments which include a linking arm are preferred. The parameters describing Y in these various instances are set forth herein.

Convenient linking arms useful in conjugation of the haptens prepared according to the method of the invention are of the general formula: —X—CO—L, wherein X is a hydrocarbylene of 3-19C in which 1-3 nonadjacent $CH_2$ may optionally be replaced by NR, S, or O (R is H or alkyl, C1-6), and wherein L is a leaving group, such as OR, $NHNH_2$, or $N_3$, or can be converted to a leaving group. The linking arm is preattached to the relevant monosaccharide or disaccharide before incorporation into the oligosaccharide to be produced. For example, in the illustrated tetrasaccharides of the invention, the acetyl glucosamine monosaccharide (or its protected or derivatized precursor) is incorporated into the product with the linker conjugated to the oxygen in position 1. In analogous oligosaccharides prepared using the intermediate blocks of the invention, linking arm-conjugated mono- or disaccharides are employed as appropriate.

Therefore, although the above embodiment of the linking arms of the invention has been defined rather generally, alternative linkers could also be used, so long as they do not contain groups which are reactive with the saccharide moieties or which interfere with the synthetic reactions to form the oligosaccharides. The use of the above derivatized carboxyl group as the functional group for attachment to the solid support or other desired conjugate is convenient, and a particularly preferred leaving group is OR, i.e., the ester, particularly the methyl ester. The ester can, however, be converted to contain an alternative leaving group such as —$NHNH_2$ or —$N_3$ after the oligosaccharide is synthesized.

A preferred embodiment for X is a straight chain alkylene of the formula $(CH_2)_n$, wherein n is 3-19. Exemplified herein is the linking arm wherein n is 8; however this is simply a choice of convenience. The spacing between the antigenic moiety and the remainder of the conjugate may be manipulated by adjusting the size of the linker. For use as an immunoadsorbent, the spacing generated by a linking arm of this formula wherein $X=(CH_2)_{6-9}$ may be particularly advantageous.

In two convenient applications, the hapten moiety may be conjugated to a solid support to serve as an immunoadsorbent or to an antigen-forming carrier to serve as an immunogen. The linking arms are useful, but not always entirely necessary in conjugating the hapten to the support or carrier. It is preferred to employ a linking arm because suitable reactivity of the linker makes conjugation more convenient, but perhaps more important, because the linking arm provides desired spacing between the hapten and support or carrier.

A variety of solid supports may be used for the first purpose, especially aminated supports such as those derived from silica gel, various organosiloxane derivatives, derivatized polyacrylamide or other resins, controlled pore glass, agarose and derivatized alumina. Other solid supports consistent with the chemical nature of the antigen can also be employed.

Suitable antigen forming carriers include proteins, such as the appropriate serum albumin, such as human or bovine serum albumin, keyhole limpet hemacyanin, tetanus toxoid, and the like. A variety of carriers which do not themselves raise interfering antibodies in the particular host is known in the art.

If the saccharides of the invention are to be used in assays, they may also be supplied in labeled form.

Suitable labels include radioisotopes such as $^{32}P$ or $^{125}I$, fluorophores such as fluorescein or dansyl, chromophores and enzymes. Means to conjugate the hapten to label are known in the art, and may include the use of the above linking arms.

B. Synthetic Methods

Figure 44:
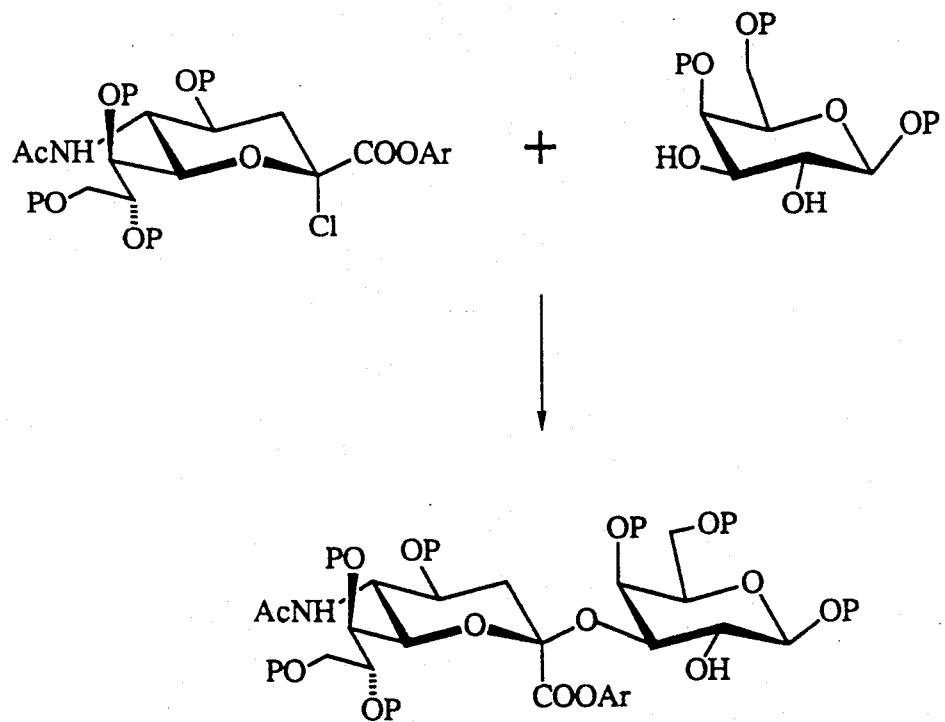
FIG. 44 shows the formation of the α (2-3) sialyl block of the invention.

The tetrasaccharide and trisaccharide haptens of the invention containing sialyl α (2-3) glycosides are obtainable in practical quantities for the first time, due to the availability of a block intermediate prepared by the method of the invention. The preparation of this block is shown in FIG. 44. It is an α (2-3) linked sialylgalactopyranoside and the preferential preparation in the α anomeric form uses reaction of a suitably derivatized sialyl halide with galactopyranosyl acceptor. The improvement in results over the methods of the prior art resides at least in part in the use of a benzyl or phenacyl ester of the sialyl residue in place of the methyl ester used previously. The presence of this derivatizing group preferentially results in the α anomer.

The intermediate block compound is shown herein in various protected forms as compounds 14, 15, 16, 18, 19, 20, 21 and 22. Compounds 14–16 are the 1-acetyl derivatives of the galactopyranoside; compounds 18–21 are the O-allyl or halide derivatives. Illustrative preparation of these various forms of the intermediate block are set forth in Examples IV, V, and VI of the herein application.

As shown in FIG. 44, a suitably protected form of the O-allyl or O-acetyl galactopyranoside is reacted with an aromatic ester, e.g., the benzyl ester of the polyacetylated (or otherwise protected) sialyl chloride. The resulting block intermediate is prepared in the α anomeric configuration in 47% total yield with only traces of the undesirable β anomer using the acetylated acceptor in Example IV and in 39% yield using the O-allyl galactopyranosyl receptor in Example V. In both cases, the benzyl ester of the sialyl halide is used as reagent.

The formation of the disaccharide block illustrated in FIG. 44, permits its subsequent reaction to form a variety of saccharide moieties, including the tri- and tetrasaccharides of the invention.

Figure 45:
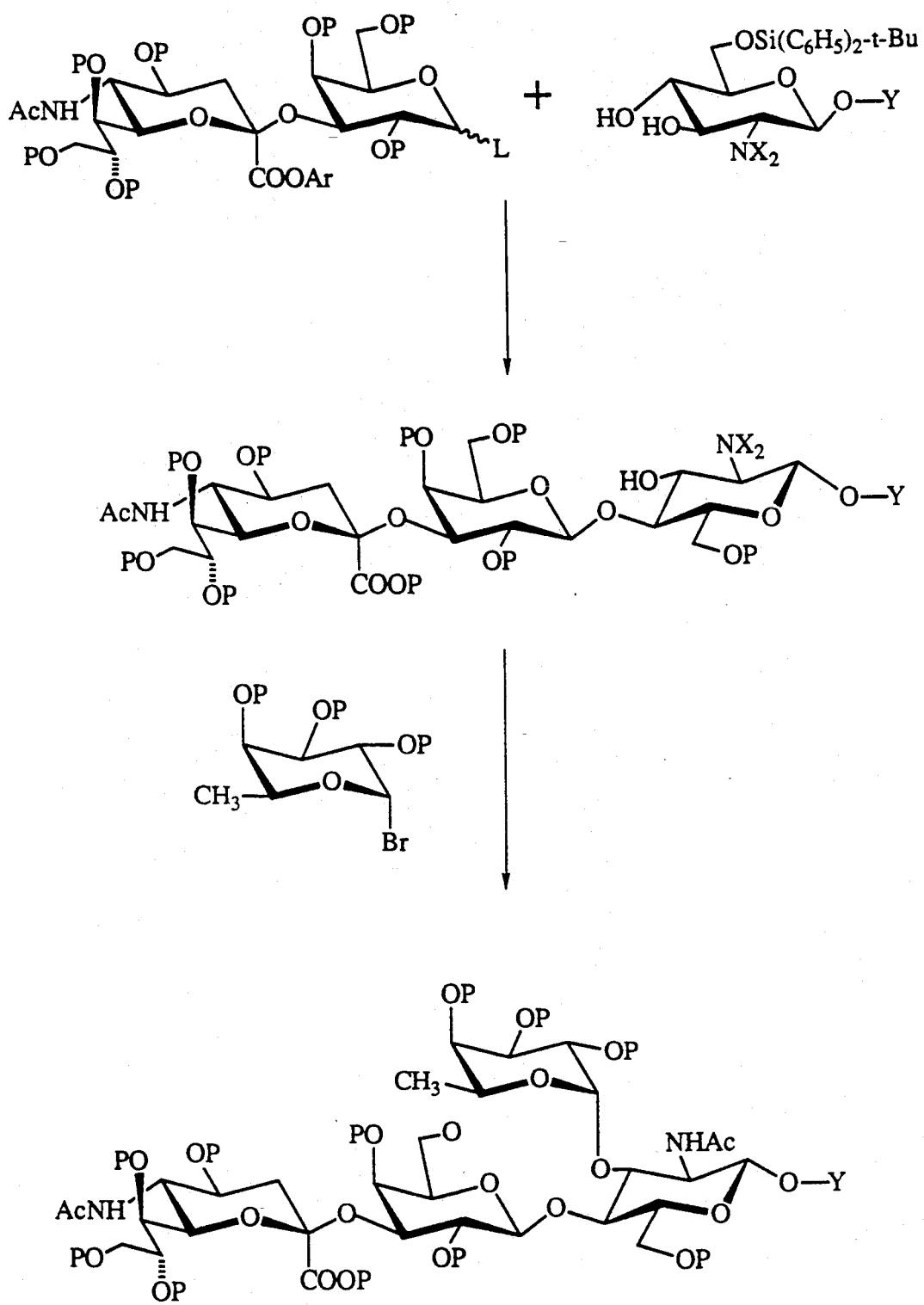
FIG. 45 shows the synthetic scheme for the production of sialo-X.
Figure 46:
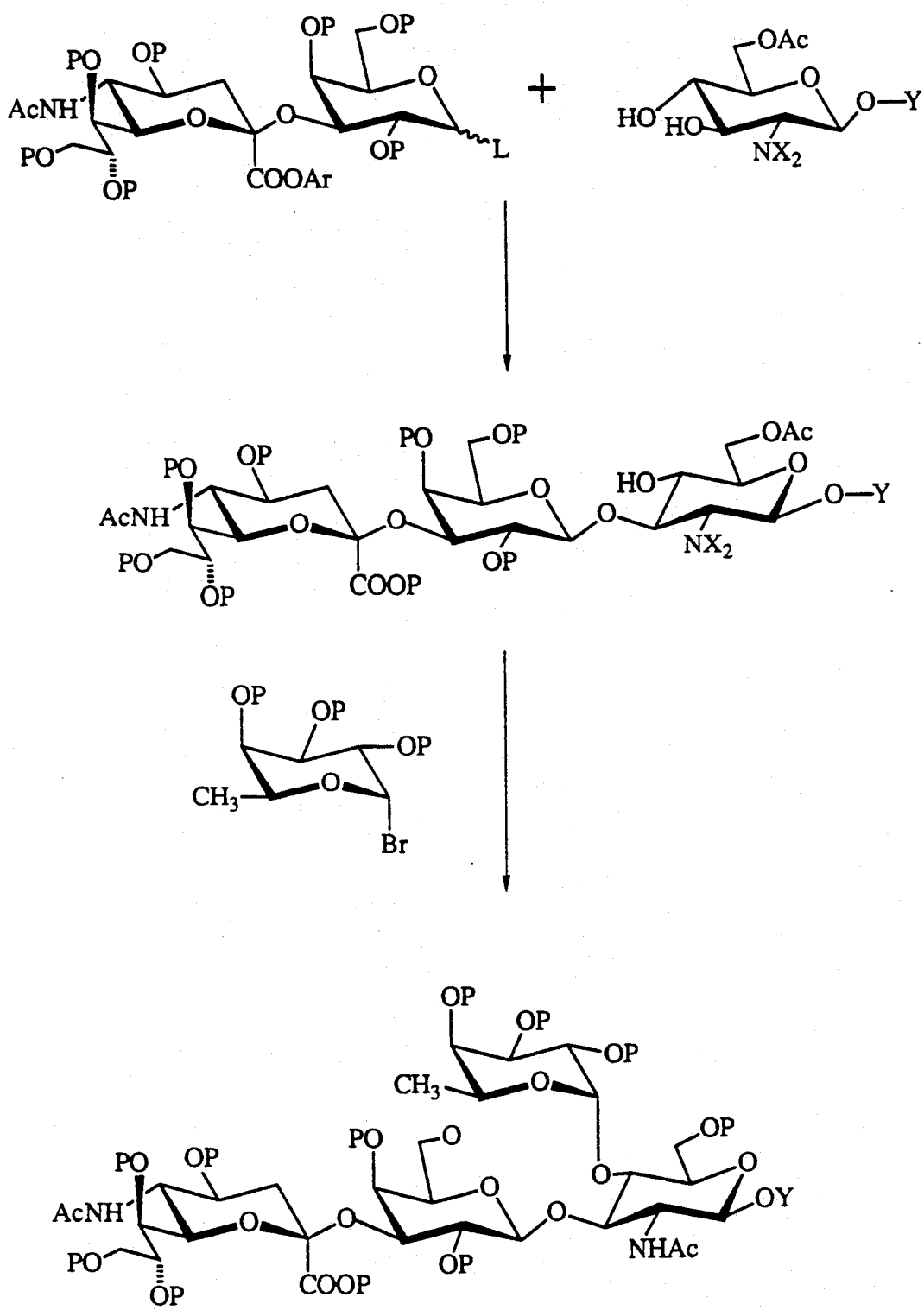
FIG. 46 shows the synthetic scheme for the production of 19-9.

FIGS. 45 and 46 illustrate the use of the intermediate block to obtain trisaccharide precursors. The trisaccharide precursors are deblocked to give the trisaccharide product compounds. These are in turn converted. As shown in FIG. 45, a suitably protected form of the block is reacted with the 3,4 diol of a glucosamine derivative which contains a silyl-derived protecting group in the 6-position. This reaction is conducted in a nonpolar dry solvent in the presence of trimethylsilyl trifluoromethane sulfonate, added portion-wise over approximately one hour.

The reaction continued to completion over another approximately one hour. The use of this acceptor, having a t-butyldiphenylsilyl protecting group in the 6-position, surprisingly, favors the formation of the desired $\beta$ (1-4) linkage. This result is unexpected in view of the steric factors. The resulting trisaccharide is then reacted with suitably protected fucopyranosyl bromide. This is freshly prepared from the protected fucopyranose. The reaction occurs under conditions generally known in the art. The resulting compound having the backbone structure of sialo-X is then deprotected as required.

The procedure for preparation of a 19-9 as shown in FIG. 46, is similar, except that the acceptor used, which has a different protecting group at the 6-position which, although sterically less significant, favors the formation of a trisaccharide with the $\beta$ (1-3) linkage. Reaction conditions and catalysts are similar.

As shown in FIGS. 45 and 46, P represents a hydrogen or a protecting group as required and Y usually represents hydrogen, alkyl (1-6C), a linking arm or another saccharide, but could also include a solid support, antigen-forming carrier or label. $X_2$ is used to indicate that the nitrogen of glucosamine can be in the form either of an azide or an acylated amino where acyl (Ac) is C1-6. Conversion of the azide to the protected amino form is conducted at a convenient point in the synthesis.

Figure 47:
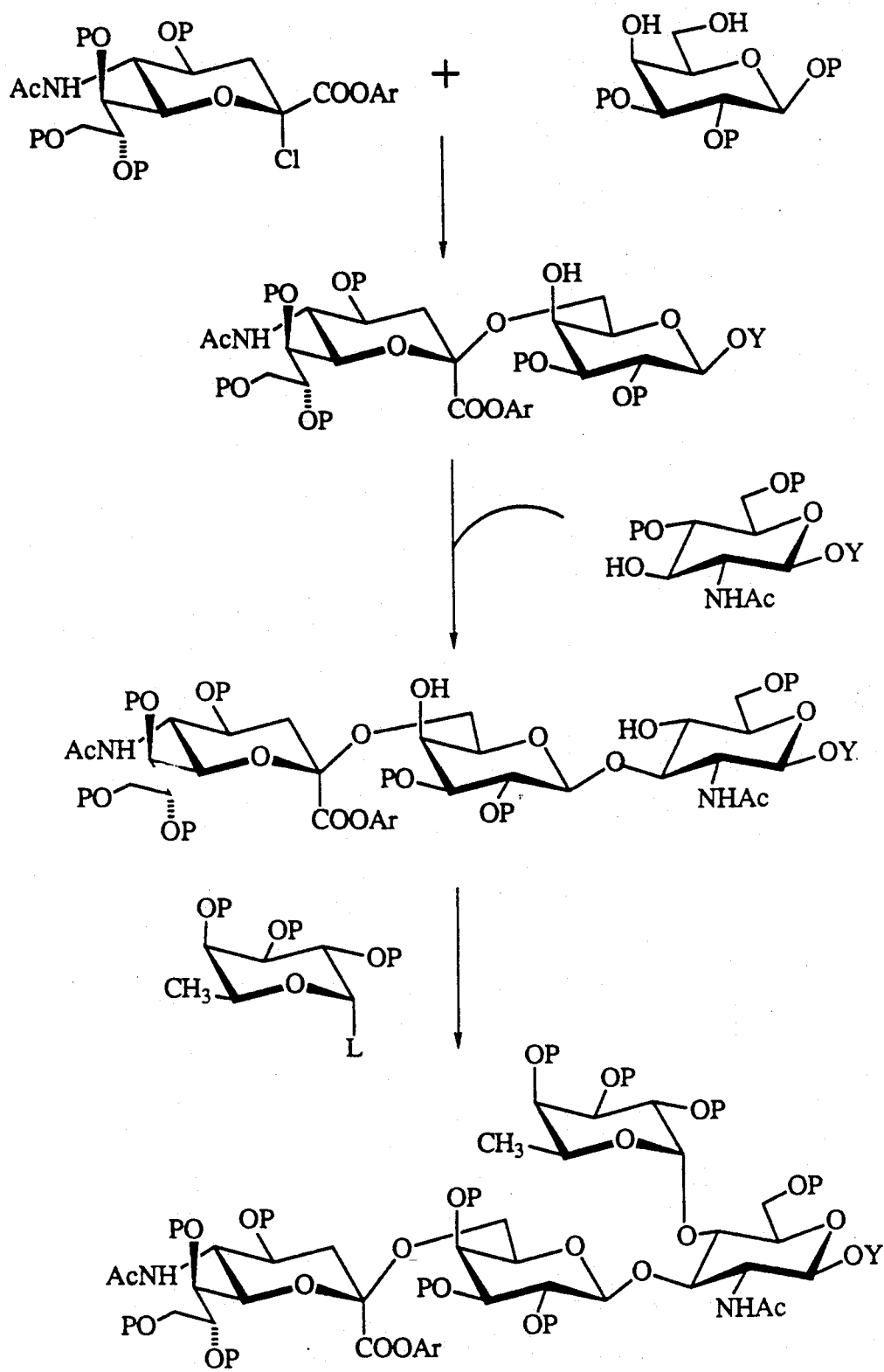
FIG. 47 shows the formation of the α (2-6) sialyl block of the invention, and its use in synthesis.

A block intermediate for the 2-6 linked sialyl galactopyranosides is prepared in a manner analogous to that shown in FIG. 44, except that the galactopyranosyl derivative is protected in the 3, 4 and 5 positions and has a free hydroxyl at position 6. This synthesis is shown in FIG. 47. Further conversion of this block intermediate to higher saccharides is analogous to that described for the $\alpha$ (2-3) sialyl block.

C. Utility of the Synthetic Haptens

The 19-9 and sialo-X haptens are known to be associated with malignant tissue. Accordingly, antibodies raised against these antigens are useful in diagnosis and therapy. The antigens obtained from these haptens of the invention are useful in producing such antibodies, and immunoadsorbents prepared from the haptens are useful in isolating, purifying, and detecting them. The trisaccharide intermediates can be used in analogous ways. In addition, they are useful as substrates for assessment of the activity of the relevant glycosyltransferases. The level of activity of the transferases is of diagnostic significance as well. For determination of transferase activity, the sample is contacted with the invention trisaccharides in the presence of a suitable monosaccharide acceptor and the decrease in concentration of the trisaccharide(s) or increase in concentration of tetrasaccharide(s) is detected.

In one application, the haptens of the invention are conjugated to an antigen-forming carrier and used to obtain large quantities of antisera immunoreactive with the antigens. Standard immunization protocols are used to prepare antisera in mammalian subjects such as mice, rabbits, or large animals such as sheep. Humans may also be used as subjects if it is intended that the antibodies be used in therapy, to prevent interspecies immune reactions. The antisera are harvested and used directly, or, if desired, the peripheral blood lymphocytes or spleenocytes of the immunized subject may be harvested for immortalization. The resulting monoclonal-secreting cell lines form specific antibodies of high affinity and specificity. An adequate supply of hapten is required not only to obtain the immunogen, but also in order to assay preparations for the production of the desired antibody. In such assays, the haptens or antigens may be used in labeled form.

In a further application, the haptens of the invention may be conjugated to a solid support in order to isolate and purify antibodies from the antisera. In this method, the hapten moieties are conjugated to the chromatographic support solid, such as those set forth above, and the sample from which the antibodies are to be isolated is applied to the support which is preferably configured as a chromatographic column. The antibodies are specifically adsorbed from the sample, and eluted by salt gradients, pH shifts or other methods known in the art.

The adsorption to and elution from chromatographic support results in isolation of or removal of antibodies from a sample, as desired, and also in their purification.

In still another application, the haptens are useful as assay tools. In the most simple application, they can be used to assess the presence and amount of antibody in a sample such as a plasma or blood sample, or in a sample extracted from tissue. This is an essential concomitant tool in the preparation and assay of antisera and monoclonal antibodies specific for the antigens, as well as a tool in diagnosis of relevant parameters such as enzyme levels (sialyl $\alpha$ (2-3) trisaccharides) or malignancy (tetrasaccharides).

A variety of immunoassay techiques are available and known in the art for use in detecting antibodies. In a typical approach, the antigen is used to coat multi-well plates to which a sample suspected of containing the antibody is applied. After the plates are washed, an additional labeled antibody specific for the species to which the sample-contained antibodies belong is added to assess the retention of antibodies from the sample in the wells. Alternatively, the antigen, labeled as described above, can be used to detect the antibodies directly, or can be used in competitive immunoassays to measure antigen levels. In this latter approach, the haptens or antigens of the invention are conjugated to label and mixed with sample in competition with analyte contained therein for the relevant antibodies.

A variety of other protocols and variations of assays which depend for their specificity on antigen/antibody binding are known in the art and are permitted by use of the haptens of the invention or the antibodies generated therefrom.

With respect specifically to the trisaccharide compounds 27 and 30, which are the biological precursors of the 19-9 and sialyl-X structures respectively, these haptens and their antigens and the immunosorbents can be used to study the nature of the reactivities of antibodies that have affinities for the larger structures. They can also be used to study the reactivities of the fucosyl transferases that act on the natural terminal structures to produce the terminal tetrasaccharides that confer the reactivities of the 19-9 and sialyl-X oligosaccharides. Assay systems that include the synthetic hapten coated on plastic which is incubated with serum samples, cellular and tissue extracts or other biological preparations in the presence of fucosyl donors that are labeled can be used to study the presence of such transferases. This method can be used to quantify fucosyl transferases. The synthetic trisaccharidic haptens themselves can be used as soluble acceptors in similar reactions and the product tetrasaccharides can be isolated and quantified by physical methods.

EXAMPLES

The examples below illustrate but do not limit the scope of the invention.

Examples I and II demonstrate the synthesis of the derivatized sialic acid halides, compounds 3, 5, and 6, through the use of the benzyl and phenacyl esters and the conversion of the per-O-acetylated derivatives into the halides.

Example III relates to the formation of α (2-6) linkage. In this reaction, the α anomer is formed exclusively when the phenacyl ester of the sialosyl chloride 5 is used whereas when the corresponding methyl ester is used, an α/β ratio of near 2/1 is obtained.

The improved anomeric control obtained when the benzyl or phenacyl ester of the sialosyl halide is used as a reagent is applied to the synthesis of the desired α (2-3) linked block in Example IV. Compound 14, a protected form of the block, is obtained by reaction of the benzyl ester 3 with the diol 13 of the derivatized galactose unit. Compound 14 is produced in 47% yield with only traces of the undesirable β anomer or of the 2-2 sialoside. The formation of this structure is central to the total synthesis of the 19-9 and sialo-X structures, and of other oligosaccharides containing the 2-3 linkage. Compound 14 is converted into compounds 15 or 16 which serve as the desired sialo (2-3) α-anomeric blocks. It can be used directly in subsequent glycosylations to give the extended structures in high yield.

Example V shows an analogous synthesis of the intermediate wherein the acceptor structure is the allyl glycoside of galactose 17. Reaction with the benzyl ester 3 leads to the activated block disaccharide 20. Example VI demonstrates the use of this block to obtain the trisaccharide 22 which is a unit present in $G_{Ms}$, $G_{Ml}$, and $G_D$ structures.

Examples VII and VIII continue the synthesis directed to the desired tetrasaccharides. These examples describe the synthesis of the linear trisaccharides 27 and 30 and derivatized forms of these compounds that are useful for the synthesis of the desired tetrasaccharides 35 and 37. Example VII details the preferred method for forming the (1-3) linkage between the block and a glucosamine derivative that is an intermediate in the synthesis of 19-9, compound 35. Example VIII shows the preferred method for the synthesis of the analogous trisaccharide having a (1-4) linkage that is a precursor for the production of the sialo-X tetrasaccharide, compound 37.

Although both intermediate trisaccharides (the (1-3) and the (1-4) are produced using the common (2-3) block disaccharides with acceptor structures 23 and 31, each of which is a 3,4-diol, the ratio of 1-3 and 1-4 linkages formed is reversed depending on the choice of derivatized acceptor. The acceptor 23, acetylated at position 6, favors (1-3); the acceptor 31, with the t-butyl (diphenyl) silyl group at position 6, favors (1-4), a surprising result in view of the steric factors.

Examples IX and X detail the synthesis of the desired tetrasaccharides from the trisaccharide intermediates. The resulting 19-9 and sialo-X are converted into synthetic antigens and immunoadsorbents as described in Examples XI and XII respectively.

Example XIII demonstrates the use of these antigens for the detection of antibody. The use of the synthetic haptens and glycoconjugates as inhibitors in this example demonstrates the potential for using this assay format for the detection of natural 19-9 structures through the inhibition of anti-19-9 reactive antibodies with the bound synthetic glycoconjugates.

EXAMPLE I

Benzyl 5-acetamido-4,7,8,9-tetra-O-acetyl-2-chloro-2,3,5-trideoxy-β-D-glycero-D-galacto-2-nonulopyranosylonate (3)

Acetic anhydride (13.5 g, 13.2 mmol) and some dimethylaminopyridine were added to N-acetyl neuraminic acid (1) (5 g, 16.1 mmol) in pyridine (25 ml). After stirring overnight at 22° C., TLC (chloroform:methanol:water 65:35:8) indicated a complete reaction. After addition of some methanol (10 ml) the mixture was stirred for 1 hour and co-evaporated with an excess of toluene. The residue was dissolved in ethyl acetate and treated with some Dowex 50 resin (H+, 20 ml). The product which was recovered after filtration, evaporation and drying in vacuo, was used directly in the next step.

Potassium fluoride (2.3 g, 39.6 mmol) followed by benzyl bromide (4.00 g, 23.4 mmol) were added to the above material (8.40 g) in dimethylformamide (85 ml). After stirring overnight at 22° C. the solvent was evaporated in vacuo, the residue taken in dichloromethane, filtered and washed with water (three times). The recovered crude product was chromatographed on silica gel (250 g) using a mixture of hexane, ethyl acetate and ethanol (6:4:1) giving the benzyl ester 2 as an α/β mixture (14:86, 8.25 g, 84%). The pure α and β anomers could be obtained through chromatography and were characterized as follows.

α anomer (foam): $[\alpha]^{22}_D$ +20.3°(c1.0, chloroform); $^1$H-nmr: 7.30(m, 5H, aromatics), 5.293(dd, 1H, $J_{6,7}$ 2.5 Hz, $J_{7,8}$ 7.0 Hz, H-7), 5.138(m, 3H incl. NH, PhCH and H-8), 5.038(d, 1H, $J_{gem}$ 12.5 Hz, PhCH), 4.893(ddd, 1H, $J_{3e,4}$ 4.6 Hz, $J_{4,5}$ 10.4 Hz, $J_{3a,4}$ 11.6 Hz, H-4), 4.670(dd, 1H, $J_{5,6}$ 11.0 Hz, H-6), 4.288(dd, 1H, $J_{8,9a}$ 2.7 Hz, $J_{9a,9b}$ 12.5 Hz, H-9a). 4.088(m, 1H, H-5), 3.988(dd, 1H, $J_{8,9b}$ 5.5 Hz, H-9b), 2.485(dd, 1H, $J_{3e,3a}$ 14.0 Hz, H-3e), 2.060, 2.108, 1.990, 1.968, 1.965, 1.818(6s, 19H, 5 OAc, 1 NAc, H-3a).

Anal. Calc. for $C_{28}H_{35}O_{13}N$: C, 56.65; H, 5.94; N, 2.36. Found: C, 56.52; H, 5.88; N, 2.15.

β anomer: m.p. 128° C.; $[\alpha]^{22}_D$ −29.5° (c1.0 chloroform); $^1$H-nmr: 7.35(m, 5H, aromatics), 5.375(dd, 1H, $J_{6,7}$ 2.0 Hz, $J_{7,8}$ 5.6 Hz, H-7), 5.263(m, 3H incl. NH, H-8 and PhCH), 5.168(d, 1H, $J_{gem}$ 12.0 Hz, PhCH), 5.093(ddd, 1H, $J_{8,9a}$ 2.6 Hz, $J_{8,9b}$ 6.5 Hz, H-8), 4.450(dd, 1H, $J_{9a,9b}$ 13.0 Hz, H-9a), 4.138(m, 3H incl. H-5, H-6 and H-9b), 2.253(dd, 1H, $J_{3e,4}$ 5.0 Hz, $J_{3e,3a}$ 13.5 Hz, H-3e), 2.125, 2.113(two), 2.025(two), 1.895(19H, 5 OAc, 1 NAc, H-3a).

Anal. Calc. for $C_{28}H_{35}O_{13}N$: C, 56.65; H, 5.94; N, 2.36. Found: C, 56.58; H, 5.82, N, 2.18.

Concentrated hydrochloric acid (1.3 ml) was added dropwise to the cooled ($-20°$ C.) solution of compound 2 (5.28 g, 8.66 mmol) and acetyl chloride (11.73 g, 10.7 ml, 14.9 mmol) in dichloromethane (25 ml). The mixture was stirred at 22° C. overnight in the tightly closed flask. TLC (chloroform, acetone 3:2) indicated a complete reaction. After cooling, the flask was opened and the content diluted with cold dichloromethane (100 ml) and quickly washed with cold water (20 ml), a cold solution of sodium bicarbonate (20 ml), cold water (20 ml) and brine (20 ml). Drying over magnesium sulfate at 5° C. and evaporation of the solvent left the crude material 3 (5.07 g, 98%, foam) which showed very little impurity ($^1$H-nmr) and was used directly as described in Example IV.

$^1$H-nmr: 7.40(m, 5H, aromatics), 5.395(dd, 1H, $J_{6,7}$ 2.4 Hz, $J_{7,8}$ 6.4 Hz, H-7), 5.322 (ddd, 1H, $J_{3e,4}$ 4.8 Hz, $J_{3a,4}=J_{4,5}$ 10.9 Hz, H-4), 5.305 (d, 1H, $J_{gem}$ 12.5 Hz, PhCH), 5.155(d, 1H, PhCH), 5.105(ddd, 1H, $J_{8,9a}$ 2.6 Hz, $J_{8,9b}$ 6.2 Hz, H-8), 4.343(dd, 1H, $J_{9a,9b}$ 12.4 Hz, H-9a), 4.293(dd, 1H, $J_{5,6}$ 9.7 Hz, H-6), 4.135(m, 1H, H-5), 4.012(dd, 1H, H-9b), 2.770(dd, 1H, $J_{3a,e}$ 14.5 Hz,H-3e), 2.282 (dd, 1H, H-3a), 2.115, 2.040 (two), 2.013, 1.902 (15H, 4 OAc, 1 NAc).

EXAMPLE II

Phenacyl 5-acetamido-4,7,8,9-tetra-O-acetyl-2-chloro-2,3,5-trideoxy-D-glycero-β-D-galacto-2-nonulopyranosylonate (5)

N-Acetylneuraminic acid (1) (2.0 g, 6.47 mmol) was treated at ambient temperature with pyridine (9 mL) and acetic anhydride (3 mL) with a catalytic amount of dimethylaminopyridine for 16 h. The originally cloudy suspension goes clear in time. TLC developed with ethyl acetate:methanol 4:1 shows the reaction is complete. The solvents were removed by evaporation under high vacuum to yield a light brown residue which was dissolved in ethyl acetate (~20 mL) and IR-120(H+) resin (5 mL) added and stirred for 5 minutes. Filtration and evaporation of the filtrate gave the crude product (3.360 g).

The crude per-O-acetylated N-acetylneuraminic acid (2.89 g, 5.49 mmol) was dissolved in anhydrous dimethylformamide (50 mL) to which was added anhydrous potassium fluoride (0.710 g, 12.27 mmol) and recrystallized phenacyl bromide (1.70 g, 8.54 mmol). TLC examination with hexane:ethyl acetate: ethanol 6:4:1 development on silica gel showed the reaction to be complete in 0.5 to 1.0 hours. The reaction mixture evaporated to give a residue (4.74 g) was taken up in dichloromethane, filtered and the filtrate evaporated.

Column chromatography on silica gel (75 g) eluted with hexane:ethyl acetate:ethanol 6:4:1 gave compound 4 (2.437 g). This represents a 62% yield based on the amount of N-acetylneuraminic acid used. Other products that are produced and separated from the per-O-acetylated phenacyl ester appear to be a very small amount of the α-anomeric acetate and a small amount of 2,3 unsaturated compound.

$^1$H-nmr: 7.90, 7.55(2 m,5H, aromatics), 5.56(s, 2H, —OCH$_2$CO), 4.60(dd, 1H, J 2,3 Hz, J 13.0 Hz, H-9), 2.66(dd, 1H, $J_{3a,3e}$ 14.0 Hz, $J_{3e,4}$ 5.6 Hz, H-3e), 2.37(t, 1H, J 11.0 Hz, H-3a).

Compound 4 (0.60 g) was treated with glacial acetic acid saturated with hydrogen chloride (25 mL, 4° C.) for 3.5 h. TLC examination of the reaction mixture developed with ethyl acetate:hexane 3:1 showed the reaction to be complete. The mixture was diluted with toluene (20 mL) and evaporated to dryness under vacuum. The residue so obtained was column chromatographed on silica gel (15 g) eluted with above solvent mixture to yield compound 5 (0.40 g) in 69% isolated yield, $^1$H-nmr: 7.92, 7.64, 7.52 (3 m,2H,1H,2H, aromatics) 5.59(d, 1H, $J_{gem}$ 16.0 Hz, —OCH$_2$—CO) 4.42(d, 1H, —OCH$_2$CO), 4.36(bd, 1H, $J_{NH,5}$ 10.0 Hz, NHAc), 4.21(m, 1H, H-4), 2.87(dd, 1H, $J_{3e,4}$ 5.0 Hz, H3e), 2.46(dd, 1H, $J_{3e,3a}$ 14Hz, $J_{3a,4}$ 11.5 Hz, H-3a), 2.16, 2.09, 2.06, 2.05, 2.05 (5 s, 5 Ac).

Phenacyl 5-acetamido-4,7,8,9-tetra-O-acetyl-2-bromo-2,3,5-trideoxy-D-glycero-β-D-galacto-2-nonulopyranosylonate (6)

The purified per-O-acetylated phenacyl ester of sialic acid 4 (0.051 g, 0.079 mmol) was treated at ambient temperature with commercial glacial acetic acid saturated with hydrogen bromide, for a period of 0.5 h. At that time the solution was diluted with toluene and evaporated under vacuum. This crude product was column chromatographed on silica gel (7.0 g), eluted with ethyl acetate:hexane 3:1 to afford the pure compound 6 (0.025 g) in 47% yield as a clear syrup:$^1$H-nmr: 7.92, 7.64, 7.52, (3 m, 5H, aromatics), 5.62 (d, 1H, $J_{gem}$15.5 Hz, —OCH$_2$CO—), 5.52(dd, 1H, $J_{7,8}$ 7.0 Hz, H-7), 5.42(d, 1H, —OCH$_2$CO—), 5.38 (d, 1H, $J_{NH,5}$ 9.2 Hz, NHAC), 5.19 (m, 1H, H-8), 4.45(dd, 1H, $J_{8,9a}$ 2.9 Hz, $J_{9b,9a}$ 9.6 Hz, H-9a), 4.33 (dd, 1H, $J_{6,7}$ 2.2 Hz, H-6), 4.29(dd, H, J 10.2 Hz, H-5, 4.06 (dd, 1H, $J_{8b,9}$ 5.5 Hz,H-9b), 3.00 (dd, 1H, $J_{3e,4}$ 4.5 Hz, $J_{3e,3a}$ 14.0 Hz, H-3e), 2.44 (dd, 1H, $J_{3a,4}$ 11.0 Hz, H-3a), 2.15, 2.09, 2.06, 2.04, 1.93, (5 s, 15H, 5 Ac).

EXAMPLE III

8-Methoxycarbonyloctyl (methyl 5-acetamido-3,5-dideoxy-D-α-glycero-D-galacto-2-nonulopyranosylonate)-(2-6)-β-D-galactopyranoside (9)

A mixture of 8-methoxycarbonyloctyl-2,3-di-O-benzoyl-β-D-galactopyranoside (7) (0.056 g, 0.101 mmol), silver trifluoromethanesulfonate (0.003 g, 0.011 mmol), silver carbonate (0.068 g, 0.248 mmol) 4° A. molecular sieves (0.200 g, powdered), and dry dichloromethane (2 mL) was cooled to $-20°$ C. under a nitrogen atmosphere. The chloride 5 (0.060 g, 0.100 mmol) dissolved in dichloromethane was added to the above mixture. The resulting mixture was allowed to warm to $-10°$ C. and held there for 1 h at which time TLC developed with ethyl acetate:hexane 4:1 showed no apparent consumption of halide or alcohol. The mixture was allowed to warm to ambient temperature over a period of 4 hours. The reaction was observed to proceed slowly at ambient temperature and over a 15 h period all of the chloride 5 and a large portion of the alcohol 7 were consumed. A new major compound was produced which travelled slightly slower then the chloride when the plate was developed with hexane:ethyl acetate:ethanol 10:10:1. At that time the mixture was filtered and the filtrate evaporated to dryness to give a white foam (0.111 g). This material was column chromatographed (7 mm I.D., 35 mm) on silica gel (~10 g) (200 psi, 1.5 min fractions) eluted with hexane:ethyl acetate:ethanol 10:10:1. The major fraction (f11-14) provided the product (0.086 g). Analysis of a 200 MHz $^1$Hmr spectrum of this material showed it to be a single glycoside of purity greater the ~95%. The only contaminant observable was the 2,3-ene compound resulting from elimination of the 3-deoxy-2-chloro compound. The yield of this single glycoside, compound 8 based on alcohol used was 70–72%: $^1$H-nmr: 5.78 (dd, 1H, $J_{1,2}$ 8.0 Hz,H-2), 5.50 (dd, 2H, $J_{gem}$ 14 Hz, OCH$_2$CO—), 4.67 (d, 1H, H-1), 3.12 (d, 1H, $J_{4,OH}$ 5.5 Hz, OH), 2.78 (dd, 1H, $J_{3'e,4'}$ 4.7 Hz, $J_{3'e,3'a}$ 12.5 Hz, H-3'e), 2.18, 2.04, 1.98, 1.93, 1.91 (5 s, 15H, 5 Ac).

The proof that this blocked phenacyl ester glycoside was the desired α-anomer was directly obtained by treating a portion of the product (5 mg) with sodium methoxide in methanol. This effected removal of the ester blocking groups and transesterification of the phenacyl ester to provide the methyl ester. De-ionization and removal of the resin by filtration and evaporation of the filtrate gave a residue. Analysis of a 200 MHz $^1$Hmr spectrum of this material showed it to be identical to that of 8-methoxycarbonyloctyl (methyl 5-acetamido-3,5-dideoxy-D-α-glycero-D-galacto-2-nonulopyranosonate)-(2-6)-β-D-galactopyranoside (9). As both anomeric (2-6) methyl ester glycosides have been prepared and their $^1$Hmr spectra fully assigned in the literature compound 8, when deblocked and transesterified, must be the α-anomer. The spectrum of the transesterified deblocked product showed no evidence of the presence of the β-anomer. The $^1$Hmr (D$_2$O) of the product contained the following easily assignable peaks: 4.38 (d,1H, $J_{1,2}$ 7.5 Hz, H-1), 3.88(s, 3H, CH$_3$), 3.69 (s, 3H, CH$_3$), 2.74(dd, 1H, $J_{3'e,3'a}$ 12.5 Hz, $J_{3'e,4'}$ 4.5 Hz, H-3'e), 2.04 (s, 3H, NHAc), 1.86 (t, 1H, $J_{3'a,4'}$ 12.5 Hz, H-3'a).

EXAMPLE IV

Preparation of Block Units, Compounds 15 and 16

1-O-acetyl-4,6-O-paramethoxybenzylidene-β-D-galactopyranose (13).

Tetra-O-benzyl galactopyranose 10 (4.00 g, 7.41 mmol), dicyclohexycarbodiimide (4.90, 24.01 mmol) and a small amount of cuprous chloride were heated at 85° C. for one hour. After cooling in ice, acetic acid (1.4 ml) in dimethoxyethane was added dropwise to the mixture which was stirred for one hour at 22° C. A solution of oxalic acid dihydrate (3.20 g, 25.0 mmol) in acetone (20 ml) was then added. Most of the acetone was evaporated off and the residue taken in ether and filtered. The organic solvent was washed with water, dried and evaporated leaving a residue which was crystallized from 98% ethanol giving 11 (2.34 g, 56%): m.p. 101°–102° C.; $[\alpha]^{20}_D$ +5.3° (c1.0, chloroform); $^1$H-nmr: 5.50(d, 1H, $J_{1,2}$ 8.5 Hz, H-1), 1.98 (s, 3H, O Ac).

Anal. Calc. for C$_{36}$H$_{38}$O$_7$: C, 74.29; H, 6.57. Found: C, 73.55: H, 6.37.

A suspension of 11 (2.20 g, 3:78 mmol) in acetic acid (35 ml) was hydrogenated for 3 hours at atmospheric pressure in the presence of 5% palladium on carbon. The catalyst was separated and further washed with acetic acid. Freeze drying left a crude product which was crystallized from 98% ethanol giving 12 (0.756 g, 92%): m.p. 173°–174° C.; $^1$H-nmr(D$_2$O): 5.61 (d, 1H, $J_{1,2}$ 8.0 Hz, H-1), 4.072 (dd, 1H, $J_{4,5}$ 1.0 Hz, $J_{3,4}$ 3.0 Hz, H-4), 2.20 (s, 3H, O Ac).

Anal. Calc. for C$_8$H$_{14}$O$_7$: C, 43.24; H, 6.35. Found: C, 42.93; H, 6.33.

Paratoluene sulfonic acid (0.020 g) was added to a suspension of 12 (0.370 g, 1.67 mmol) and paramethoxy dimethoxytoluene (0.344 g, 1.90 mmol) in acetonitrile (12 ml). After 0.5 hour, some triethylamine was added and the solvent evaporated in vacuo. After chromotagraphy on silicagel using a mixture of chlorform and acetonitrile (4:6), 13 was recovered as a solid (0.475 g, 82%): $^1$H-nmr(D$_6$DMSO): 7.38 and 6.43(2M, 4H, aromatics), 5.50(s, 1H, benzylidene), 5.41(d, 1H, $J_{1,2}$ 7.5 Hz, H-1), 3.76(s, 3H, O—CH$_3$), 2.10 (s, 3H, O Ac).

(Benzyl 5-acetamido-4,7,8,9-tetra-O-acetyl-3,5-dideoxy α-D-glycero-D-galacto-2-nonulopyranosylonate)-(2-3)-O-(1-O-acetyl-4,6-O-paramethoxybenzylidene-β-D-galactopyranose) (14)

A solution of silver trifluoromethanesulfonate (0.924 g, 3.60 mmol) and 2,6-di-tert-butylpyridine (0.768 g, 0.900 ml, 4.02 mmol) in tetrahydrofuran (4 ml, distilled before being used on to molecular sieves) was added to a suspension of the diol 13 (1.188 g, 3.49 mmol) in tetrahydrofuran (4 ml). Dissolution occurred after stirring. Calcium sulfate (1.50 g crushed) was added and stirring was continued for 0.5 hour at 22° C. After cooling at −78° C., the chloride 3 (2.25 g, 3.846 mmol) in tetrahydrofuran (4 ml) was syringed in slowly (1 hour). TLC (chloroform:acetone 70:30 and hexane:ethyl acetate:ethanol 15:10:1, four elutions) indicated a slow reaction. The mixture was stirred for 1 hour at −78° C., warmed up and stirred for 1 hour at −55° C. After cooling down to −78° C., more silver triflate (0.514 g, 2.00 mmol) and 2,6-di-tert-butylpyridine (0.382 g, 0.448 ml, 2.00 mmol) in tetrahydrofuran (2 ml) were added followed by a slow addition of the chloride (1.17 g, 2.00 mmol) in tetrahydrofuran (1.5 ml). After further stirring for 1 hour at −55° C., the mixture was slowly warmed up to 0° C. in about three hours. After dilution with dichloromethane (100 ml) and filtration, the solvents were washed with a solution of sodium bicarbonate, water and brine. The recovered crude product (5.74 g) was chromatographed on silica gel (240 g, 3.5×50 cm) eluted with a mixture of chloroform and acetone (75:25, containing 0.01% of pyridine). Purity of the fractions was checked by running the TLC plates in both solvent mixtures indicated above. This afforded the α-sialoside 14 (foam, 1.48 g, 47%): $[\alpha]^{22}_D$ +7.6° (c1.0 chloroform); $^1$H-nmr: 7.400(m, 7H, aromatics), 6.970(m, 2H, aromatics), 5.625(d, 1H, $J_{1,2}$ 8.0 Hz, H-1), 5.540(ddd, $J_{7',8'}$ 8.5 Hz, $J_{8',9'a}$ 2.5 Hz, $J_{8',9'b}$ 6.5 Hz, H-8'), 5.300 [m, 2H incl. PhCH(d, $J_{gem}$ 12.0 Hz) and H-7'(dd, $J_{6',7'}$ 2.5 Hz)], 5.175(d, 1H, $J_{5',NH}$ 9.5 Hz, NH), 5.075(d, 1H, PhCH), 4.975 (ddd, 1H, $J_{3'e,4'}$ 4.5 Hz, $J_{3'a,4'}$ 12.5 Hz, $J_{4',5'}$ 10.0 Hz, H-4'), 4.880(s, 1H, benzylidene), 3.900(ddd, 1H, $J_{2,OH}$ 1.5 Hz, $J_{2,3}$ 10.0 Hz, H-2), 3.787(s, 3H, OCH$_3$), 2.785 (dd, 1H, $J_{3'a,3'e}$ 14.0 Hz, H-3'e), 2.192, 2.150, 2.130, 2.050, 2.017, 1.895(6 s, 19H, 5 OAc, 1 NAc and H-3'a).

Anal. Calc. for C$_{42}$H$_{51}$NO$_{20}$: C, 56.69; H, 5.88; N, 1.60. Found: C, 56.23; H, 5.88; N, 1.60

(Benzyl 5-acetamido-4,7,8,9-tetra-O-acetyl-3,5-dideoxy-α-D-glycero-D-galacto-2-nonulopyranosylonate)-(2-3)-O-(1,2,4,6-tetra-O-acetyl-β-D-galactopyranose) (15)

Compound 14 (1.80 g, 2.02 mmol) was warmed up to 45° C. in a 10:1 mixture of acetic acid and water (60 ml). TLC (ethyl acetate:methanol 100:5) indicated the completion of the reaction in about 1.5 hours. The solution was co-evaporated with an excess of toluene and the residue dried in vacuo. Acetic anhydride (2 ml) and some DMAP were added to the above material dissolved in pyridine (25 ml). After stirring for 18 hours at 22° C., TLC indicated the completion of the reaction.

The residue obtained after evaporation of the solution with an excess of toluene was diluted with dichloromethane. The solution was washed with water, a solution of sodium bicarbonate, water and brine. The recovered syrup was combined with a material previously obtained in the same manner from 14 (1.028 g, 1.156 mmol). This crude product (3.5 g) was chromatographed on silica gel (100 g) using ethyl acetate as eluant. Pure 15 (2.62 g, 92%) was obtained as a foam, $[\alpha]^{22}_D$ +27.2° (c1.0 chloroform); $^1$H-nmr: 7.40(m, 5H, aromatics), 5.825(d, 1H, $J_{1,2}$ 8.0 Hz, H-1), 5.513(ddd, 1H, $J_{7',8'}$ 8.3 Hz, $J_{8',9'a}$ 2.5 Hz, $J_{8',9'b}$ 6.5 Hz, H-8'), 5.488(d, 1H, $J_{gem}$ 12.0 Hz, PhCH), 5.313 (dd, 1H, $J_{6',7'}$ 2.5 Hz, H-7'), 5.165(dd, 1H, $J_{2,3}$ 10.0 Hz, H-2), 5.087[m, 2H incl. PhCH($J_{gem}$ 12.0 Hz) and H-4(bd, $J_{3,4}$ 3.5 Hz)], 4.938(d,1H, $J_{5',NH}$ 10.0 HZ, NH), 4.862(ddd, 1H, $J_{3'e,4'}$ 4.5 Hz, $J_{3'a,4'}$ 12.5 Hz, $J_{4',5'}$ 10.0 Hz, H-4'), 4.787(dd, 1H, H-3), 3.533(dd, 1H, $J_{5',6'}$ 10.5 Hz, H-6'), 2.638(dd, 1H, $J_{3'a,3'e}$ 13.5Hz, H-3'e), 2.213, 2.188, 2.113, 2.088, 2.063(two), 2.043, 2.040, 1.982(8 s, 27H, 8 OAc, 1 NAc), 1.687(t, 1H, H-3'a).

Anal. Calc. for $C_{40}H_{51}O_{22}N$: C, 52.92; H, 5.66; N, 1.50. Found: C, 53.27; H, 5.92; N, 1.47.

Preparation of (benzyl 5-acetamido-4,7,8,9-tetra-O-acetyl-3,5-dideoxy-α-D-glycero-D-galacto-2-nonulopyranosylonate)-(2-3)-O-(1,4,6-tri-O-acetyl-2-O-benzoyl-β-D-galactopyranose) (16)

Benzoic anhydride (0.419 g, 1.85 mmol) and a small amount of dimethylaminopyridine were added to the starting material 14 (0.713 g, 0.801 mmol) in pyridine (5 ml). The mixture was stirred at 40° C. for 24 hours and 2 hours at 22° C. after addition of some methanol. Dilution with dichloromethane, washing with water, a solution of sodium bicarbonate and water followed by drying and evaporation of the solvents left a residue which was co-evaporated with some toluene. The crude product was chromatographed on silica gel (20 g) using a mixture of chloroform and acetone (85:15) as eluant. The pure 2-O-benzoyl disaccharide (0.710 g, 89%) was obtained.

$^1$H-nmr: 8.08(m,2H), 7.20-7.60 (m,5H) and 6.85(m,2H) all aromatics, 5.99(d, 1H, $J_{1,2}$ 8.0 Hz, H-1), 5.56[m, 2H, incl. H-2 (dd, $J_{1,2}$ 8.0 Hz, $J_{2,3}$ 10.0 Hz) and H-8'(m)], 5.22(dd, 1H, $J_{7',8'}$ 8.0 Hz, $J_{6',7'}$ 2.0 Hz, H-7'), 5.08(d, 1H, $J_{gem}$ 12.0 Hz, PhCH), 5.00[m,3H, incl. benzylidene(s), NH(d), PhCH(d)], 4.85(m, 1H, H-4'), 3.79(s, OCH₃), 2.69(dd, 1H, $J_{3'a,3'e}$ 13.0 Hz, $J_{3'e,4'}$ 4.5 Hz, H-3'e), 2.23, 2.09, 1.99, 1.97, 1.82, 1.72(6 s, 19H, 5 OAc, 1 NAc overlapping with H-3'a).

The above disaccharide (0.350 g, 0.357 mmol) was dissolved in a mixture of acetic acid and water (90:10, 10 ml) and warmed up to 45° C. for 1 hour. The mixture was co-evaporated with an excess of toluene and the residue dried in vacuo (0.695 g).

Acetic anhydride (0.300 m) and some dimethylaminopyridine were added to the above material dissolved in pyridine (4 ml). After 24 hours at 22° C., some methanol was added and the mixture worked up as usual leaving a crude material which was co-evaporated with toluene. The residue was chromatographed on silica gel using a mixture of chloroform and acetone (85:15) as eluant giving 16 (0.595 g, 88%).

$^1$H-nmr: 6.05(d, 1H, $J_{1,2}$ 8.0 Hz, H-1), 5.54(m, 1H, H-8'), 5.47(d, 1H, $J_{gem}$ 12.0 Hz, PhCH), 5.39(dd, 1H, $J_{2,3}$ 10.0 Hz, H-2), 5.17[m, 2H, incl. H-4 and H-7'), 5.08(d, 1H, PhCH), 4.92(dd, 1H, $J_{3,4}$ 3.5 Hz, $J_{4,5}$ 10.5 Hz, H-3), 4.80(m, 2H incl. NH and H-4'), 2.59(dd, 1H, $J_{3'e,4'}$ 4.0 Hz, $J_{3'e,3'a}$ 13.0 Hz, H-3'e), 2.21, 2.16, 2.12 (two), 2.00, 1.98, 1.79, 1.45 (8s, 24H, 7 OAc, 1 NAc), 1.73(t, 1H, $J_{3'a,4'}$ 12.0, H-3'a).

EXAMPLE V

Preparation of allyl (benzyl 5-acetamido-4,7,8,9,-tetra-O-acetyl-3,5-dideoxy-α-D-glycero-D-galacto-2-nonulopyranosylonate)-(2-3)-(4,6-O-benzylidene-β-D-galactopyranoside) (18)

The diol 17 (0.724 g, 2.35 mmol) obtained by well known procedures from allyl β-D-galactopyranoside, silver trifluoromethanesulfonate (0.637 g, 2.48 mmol), 2,6-di-tert-butylpyridine (0.523 g, 2.74 mmol) and calcium sulfate (0.500 g) were mixed in tetrahydrofuran (3 mL) as indicated previously for the preparation of 14 in Example IV. After cooling at −45° C., the chloride 3 11.52 g, 2.61 mmol) in tetrahydrofuran (3 mL) was syringed dropwise in about 2 hours. The mixture was stirred for 1 hour at −35° C. After cooling down to −45° C., more silver trifluoromethanesulfonate (0.318 g, 1.24 mmol), and base (0.261 g, 1.37 mmol) in tetrahydrofuran (1.5 mL) were added, followed by the chloride 3 (0.800 g, 1.35 mmol) in tetrahydrofuran (2.5 mL) as indicated above. After stirring for 1 hour at −35° C., the mixture was slowly warmed up to 0° C. A work up similar to that described above for 14 provided a crude mixture (3.9 g). Recovery of the appropriate fractions obtained after chromatography on silica gel (100 g) using a mixture of chloroform, acetone, and methanol (90:10:1) gave a mixture of the disaccharide 18 and of the product of hydrolysis of the chloride. Further chromatography of silica gel 60H using a mixture of haexane:ethyl acetate:ethanol 15:10:1 (80 g) provided 18 (0.783 g, 39%).

$^1$H-nmr 6.00(m, 1H, —CH═), 5.49(m, 1H, H-8'), 5.18 [m, 2H, incl. PhCH(d, $J_{gem}$ 12.0 Hz)], 5.07 (d, 1H, PhCH), 4.98 (s, 1H, benzylidene), 4.95 (ddd, 1H, $J_{3'e,4'}$ 4.5 Hz, $J_{3'a,4'}$ 13.0 Hz, $J_{4',5'}$ 10.0 Hz, H-4'), 2.81(dd, 1H, $J_{3'a,3'e}$ 4.5 Hz, H-3'e), 2.23, 2.17, 2.06, 2.03, 1.92 (5 s, 16H, 4 OAc, 1 NAc overlapping with H-3'e).

Preparation of Allyl (benzyl 5-acetamido-4,7,8,9-tetra-O-acetyl-3,5-dideoxy-α-D-glycero-D-galacto-2-nonulopyranosylonate)-(2-3)-(4,6-di-O-acetyl-2-O-benzoyl-β-D-galactopyranoside) (19)

Benzoylation of 18 (0.600 g, 0.7 mmol) as described above in the case of 16 gave a crude product. Chromatography on silica gel (18 g) using a mixture of chloroform and methanol (97.5:2.5) as eluant gave the pure 2-benzoyl disaccharide (0.630 g, 93%).

$^1$Hmr: 5.78 (m, 1H, —CH═), 5.44 (m, 2H, incl. H-8' and H-2(dd, $J_{1,2}$ 8.0 Hz, $J_{2,3}$ 10.0 Hz, H-2), 4.78[m, 2H, incl. H-1 (d)], 2.78 (dd, 1H, $J_{3'e,4'}$ 4.5 Hz, $J_{3'e,3'a}$ 13.0 Hz, H-3'e), 2.27, 2.08, 1.95, 1.83, 1.73 (5s, 16H, 4 OAc, I NAc overlapping with H-3'a).

The above disaccharide (0.600 g, 0.624 mmol) was hydrolyzed (95° C) and peracetylated as indicated previously for 16. The residue obtained was chromatographed on silica gel (18 g) using a mixture of chloroform and methanol (98:2) as eluant giving 19 (0.502 g, 83%).

$^1$H-nmr: 5.82 (m, 1H, —CH═), 5.60 (m, 1H, H-8'), 5.48 (d, 1H, $J_{gem}$12.0 Hz, PhCH), 5.33 (dd, 1H, $J_{1,2}$8.0 Hz, $J_{2,3}$10.0 Hz, H-2), 2.57 (dd, 1H, $J_{3'e,3'a}$13.5 Hz, $J_{3'e,4'}$ 4.5 Hz, H-3'e), 2.23, 2.13 (two), 2.08, 1.95, 1.76, 1.45, (6s, 21H, 6 OAc, 1 NAc), 1.70 (t, 1H, $J_{3'e, 4'}$ 13.0 Hz, H-3'e).

Preparation of (benzyl 5-acetamido-4,7,8,9-tetra-O-acetyl-3,5-dideoxy-α-D-glycero-D-galacto-2-nonulopyranosylonate)-(2-3)-O-(4,6-di-O-acetyl-2-O-benzoyl-β-D-galactopyranosyl chloride) (20)

Palladium dichloride (0.046 g, 0.261 mmol) was added to a mixture of the starting material 19 (0.250 g, 0.261 mmol) with sodium acetate (0.060 g, 0.726 mmol) in a mixture of acetic acid (2.5 mL) and water (0.125 mL). After 20 hours at 22° C., the mixture was diluted with methylene chloride and the catalyst separated. The solvent was washed with water, a solution of sodium bicarbonate and water. Drying and evaporation left a residue (0.240 g) which was chromatographed on silica gel (16 g) using a mixture of chloroform and methanol (97:3), to give the product (0.163 g, 67%) as an anomeric mixture ($^1$H-nmr).

A solution of oxalyl chloride (0.011 g, 0.0087 mmol in methylene chloride was added to a solution of the reducing disaccharide (0.080 g, 0.0871 mmol), dimethylformamide (0.0635 g, 0.871 mmol) in methylene chloride (2 mL) at −15° C. The mixture was slowly warmed up to −5° C. and a second portion of the chloride was added. After 0.5 hour, the temperature was brought to 0° C. and a third portion of oxalyl chloride was added. After 15 minutes at 0° C., the mixture was co-evaporated with an excess of dry toluene and dried in vacuo to give 20 (0.080 g). As indicated by $^1$H-nmr the product contained about 15–20% of impurities.

$^1$H-nmr: 5.65[m, 2H, incl. H-1(d, $J_{1,2}$8.0 Hz) and H-8'(m)], 5.49[m, 2H, incl. H-2(dd, $J_{2,3}$10.0 Hz)], 5.44 (d, 1H, $J_{gem}$12.0 Hz, PhCH), 4.95(ddd, $J_{3'e,4'}$ 4.5 Hz, $J_{3'a,4'}$ 13.0 Hz, $J_{4',5'}$ 10.0 Hz, H-4'), 2.70(dd, 1H, $J_{3'e,3'a}$12.5 Hz, H-3'e), 2.26, 2.23, 2.15, 2.14, 2.10, 1.97, 1.40, (7s, 6 OAc, 1 NAc), 1.65 (t, 1H, $J_{3'a,3'e}$12.5 Hz, H-3'a).

EXAMPLE VI

Preparation of allyl (benzyl 5-acetamido-4,7,8,9-tetra-O-acetyl-3,5-dideoxy-α-D-glycero-D-galacto-2-nonulopyranosylonate)-(2-3)-O-(2,6-di-O-acetyl-β-D-galactopyranoside) (21)

Compound 18 (0.150 g, 0.175 mmol) in pyridine (1 ml) was acetylated in the presence of dimethylaminopyridine for 24 hours at 22° C. After addition of methanol, the usual work up left a residue which was chromatographed on silica gel (8 g) using a mixture of chloroform and acetone (70:30) as eluant giving the product (0.150 g, 95%).

$^1$H-nmr: 5.90(m, 1H, —CH=, 5.57(m, 1H, H-8'), 5.37(dd, 1H, $J_{6',7'}$ 2.5 Hz, $J_{7',8'}$ 9.5 Hz, H-7'), 5.24[m, 2H incl. H-2(dd, $J_{1,2}$8.0 Hz, $J_{2,3}$9.5 Hz)], 4.90(s, 1H, benzylidene), 4.83(m, 1H, H-4'), 4.62(d, 1H, $J_{1,2}$8.0, H-1), 2.75(dd, 1H, $J_{3'e3'a}$, 4.5 Hz, $J_{3'e,4'}$ 12.5 Hz, H-3'e), 2.25, 2.22, 2.12, 2.07, 2.03, 1.88, (6s, 5 OAc, 1 NAc, overlapping with H-3'a).

The above product was heated at 95° C. for 1 hour in a mixture of acetic acid and water (9:1, 4 ml). Co-evaporation with toluene and drying in vacuo left a residue which was run through silica gel (3 g) using a mixture of chloroform and acetone (65:35) giving 0.098 g (72.5%) of the 4,6-diol.

Acetyl chloride (5.6 mg, 0.071 mmol) in methylene chloride (0.100 ml) was added to a mixture of the diol (0.057 g, 0.071 mmol), pyridine (0.0062 mg, 0.078 mmol) in dichloromethane (5 ml) and cooled to −70° C. The mixture was slowly warmed up to 0° C. for 1 hour. After cooling down to −78° C. more pyridine (0.012 g, 0.156 mmol) followed by acetyl chloride (11.2 mg, 0.142 mmol) in dichloromethane (0.200 ml) were added. The mixture was then warmed up to −15° C. and methanol added. After the usual work up followed by drying and evaporation of the solvents, the residue was chromatographed on silica gel (2.5 g) using a mixture of chloroform and acetone (75:25). Evaporation of the appropriate fractions provided the disaccharide 21 (0.043 g, 70%).

$^1$H-nmr: 5.90 (m, 1H, —CH=), 5.53(m, 1H, H-8'), 5.38(dd, 1H, $J_{6',7'}$ 2.7 Hz, $J_{7',8'}$ 9.0 Hz, H-7'), 5.20(m, 2H incl. PhCH and =CH), 5.08[m, 2H, incl. H-2(dd, $J_{1,2}$ 8.0 Hz, $J_{2,3}$ 10.0 Hz)], 4.83(ddd, 1H, $J_{3'e,4'}$ 4.5 Hz, $J_{3'a,4'}$ 13.5 Hz, $J_{4',5'}$ 10.0 Hz, H-4'), 4.53(d, 1H, H-1), 2.70(dd, 1H, $J_{3'a,3'e}$ 4.5 Hz, H-3'e), 2.18, 2.17, 2.10, 2.08, 2.06, 2.04, 1.88(7s, 22H, 6 OAc, 1 NAc overlapping with H-3'a).

Preparation of allyl (benzyl 5-acetamido-4,7,8,9-tetra-O-acetyl-3,5-dideoxy-α-D-glycero-D-galacto-2-nonulopyranosylonate)-(2-3)-O-[3,4,6-tri-O-acetyl-2-deoxy-2-phthalimido-β-D-galactopyranosyl-(1-4)-O]-(2,6-di-O-acetyl-β-D-galactopyranoside) (22)

A solution of silver trifluoromethanesulfonate (11.7 mg, 0.0456 mmol) in toluene (0.4 ml) was syringed into a mixture of the disaccharide 21 (0.013 g, 0.0152 mmol), molecular sieves 4A (0.070 mg, crushed) and 3,4,5-tri-O-acetyl-2-deoxy-2-phthalimido-β-D-galactopyranosyl chloride (0.024 g, 0.053 mmol) in dichloromethane (0.6 ml) at −35° C. The mixture was stirred for 2.5 hours at −35° C. then one hour at −20° C. After cooling at −78° C. methanol was added. The mixture was then brought to 0° C. diluted with dichloromethane, filtered and the solvent successively washed with a solution of sodium bicarbonate and water. Drying and evaporation left a residue (0.050 g) which was chromatographed on silica gel (2 g) using a mixture of hexane, ethyl acetate and ethanol (10:10:1) as eluant. Evaporation of the appropriate fractions gave 22 (0.013 g, 67%).

$^1$H-nmr: 5.84[m, 2H, incl. —CH=(m) and H-3''(dd, $J_{3'',4''}$ 3.5 Hz, $J_{2'',3''}$ 11.5 Hz)], 5.40(m, 2H incl. H-8' and PhCH), 5.13[m, 2H, incl. H-1''(d, $J_{1'',2''}$ 8.0 Hz)], 4.78(ddd, 1H, $J_{3'e, 4'}$ 4.5 Hz, $J_{3'a,4'}$13.5 Hz, $J_{4',5'}$ 10.0 Hz, H-4'), 4.60(dd, 1H, $J_{1,2}$ 8.0 Hz, $J_{2,3}$ 10.0 Hz, H-2), 4.50[m, 2H, incl. H-2''(dd) and H-1(d)], 3.02(dd, 1H, $J_{3'a,3'e}$ 13.5 Hz, H-3'e), 2.15(two), 2.14, 2.10, 2.05, 2.02 (two), 1.88, 1.87, 1.86 (8s, 30H, 9 OAc, 1 NAc), 1.40 (t, 1H, H-3'a).

EXAMPLE VII

Synthesis of Trisaccharides: Compounds 27 and 30

8-Methoxycarbonyloctyl 6-O-acetyl-2-azido-2-deoxy-β-D-glucopyranoside (23)

3,4,6-tri-O-acetyl-2-azido-2-deoxy-α-D-glucopyranosyl bromide (5 g, 0.0126 mmol) in dichloromethane (5 ml) was added dropwise in 0.5 hour into a mixture of 8-methoxycarbonyl octanol (5.0 g), molecular sieves 4A (7.5 g, crushed), dry silver carbonate (4.5 g, 0.053 mmol) in dichloromethane (5 ml) stirred and cooled at −20° C. The mixture was brought to −10° C. and stirred for 3–4 hours at which time TLC developed with hexane:ethyl acetate (60:40) indicated that the reaction was complete. The mixture was then diluted with dichloromethane, filtered on celite washed with water (twice). The crude product obtained after evaporation was dissolved in pyridine (30 ml) and acetylated with acetic anhydride (1.5 ml) at 22° C. for 48 hours. TLC indicated that the unreacted alcohol had been acetylated. Methanol was added to the mixture which was then diluted with dichloromethane washed with water, a solution of sodium bicarbonate, water and brine. The crude product was chromatographed on silica gel using a mixture of hexane and ethyl acetate (75:25) as the eluant which gave a pure product (5.5 g, 90%). The material was crystallized from ethanol: $[\alpha]^{22}_D$ −13.2° (c1.0, chloroform); m.p. 59°–61°; $^1$H-nmr: 5.00(m, 2H, H-3 and H-4), 4.39 (d, 1H, $J_{1,2}$ 7.5 Hz, H-1), 3.45–4.45[m incl. OCH$_3$(s, 3.67)], 2.10, 2.05 (2s, 6H, 2 OAc).

Anal. Calc. for $C_{22}H_{35}O_{10}N_3$: C, 52.68; H, 7.03; N, 8.38, Found: C, 52.74; H, 6.90; N, 8.42.

A 0.2N solution of sodium methoxide in methanol (0.5 ml) was syringed into a flask containing the above compound (5.5 g, 0.011 mmol) in methanol (160 ml). After 1 day at 22° C., some Dowex(H$^+$) resin was added to the solution. After stirring and filtration, evaporation of the solvent left a residue which was used directly in the next step without characterization.

Acetyl chloride (0.408 ml, 5.75 mmol) in dichloromethane (12 ml) was added dropwise (45 minutes) to a solution of the triol (4.79 mmol) and pyridine (0.462 ml, 5.75 mmol) in dichloromethane (80 ml) cooled to −78° C. After 30 minutes, TLC (ethyl acetate) indicated the completion of the reaction and some methanol was added. The mixture was diluted with dichloromethane and washed with water. The solvents were evaporated in vacuo with an excess of toluene and the residue chromatographed on silica gel (100 g) using a mixture of hexane:ethyl acetate (45:55). Pure 23 (1.71 g, 89%) was obtained as a syrup, $[\alpha]^{22}_D$ −24°(c1.0, chloroform); $^1$H-nmr: 4.33(d, $J_{1,2}$ 7.5 Hz, H-1),3.68(s, 3H, OCH$_3$), 2.15(s, 3H, OAc).

Anal. Calc. for $C_{18}H_{31}O_8N_3$: C, 51.78; H 7.49; N,10.07. Found: C, 51.42; H, 7.89; N, 10.56.

8-Methoxycarbonyloctyl (benzyl 5-acetamido-4,7,8,9-tetra-O-acetyl-3,5-di-deoxy-α-D-glycero-D-galacto-2-nonulopyranosylonate)-(2-3)-O-(2,4,6-tri-O-acetyl-β-D-galactopyranosyl)-(1-3)-O-(6-O-acetyl-2-azido-2-deoxy-β-D-glucopyranoside) (24) and 8-methoxycarbonyloctyl (benzyl 5-acetamido-4,7,8,9-tetra-O-acetyl-3,5-di-deoxy-α-D-glycero-D-galacto-2-nonulopyranosylonate)-(2-3)-O-(2,4,6-tri-O-acetyl-β-D-galactopyranosyl)-(1-4)-O-(6-O-acetyl-2-azido-2-deoxy-β-D-glucopyranoside) (25)

Trimethylsilyl trifuoromethanesulfonate (0.159 ml, 0.183 g, 0.813 mmol) in dichloromethane (2 ml) was added portionwise (1 hour) to a mixture of 15 (0.730 g, 0.813 mmol), the diol 23 (0.649 g, 1.62 mmol) and drierite (0.650 g, crushed) in dichloromethane (5 ml) at 22° C. TLC (hexane:ethyl acetate:ethanol 10:10:1) indicated that the reaction progressed rapidly after more than 0.5 equivalent of the trimethylsilyl triflate had been added. The reaction was quenched by addition of triethylamine after one hour. The mixture was diluted with dichloromethane, filtered and washed with a solution of sodium bicarbonate, water and brine. Evaporation and drying in vacuo left a residue (1.5 g).

The crude product (4.70 g) obtained from 15 (2.63 g, 2.95 mmol) was chromatographed on silica gel (140 g) using a mixture of hexane:acetone (4:6) as eluant. This separated the unreacted starting 23 (0.020 g) and other compounds from a 2:1 mixture of the two trisaccharides 24 and 25 (2.60 g, 70%). Further column chromatography on TLC grade silica gel eluted with a mixture of hexane:ethyl acetate:ethanol (30:70:1) under pressure gave the trisaccharides 24 (1.516 g) and 25 (0.794 g).

Trisaccharide 24: foam, $[\alpha]^{22}_D$ +0.188°(c1.0 chloroform); i.r. 2115 cm$^{-1}$(N$_3$); $^1$H-nmr: 7.400(m, 5H, aromatics), 5.538(ddd, 1H, $J_{7'',8''}$ 9.0 Hz, $J_{8'',9''a}$ 2.7 Hz, $J_{8'',9''b}$ 5.2 Hz, H-8''), 5.450(d, 1H, $J_{gem}$ 12.5 Hz, PhCH), 5.350(dd, 1H, $J_{6'',7''}$ 2.7 Hz, H-7''), 5.095(dd, 1H, $J_{1',2'}$ 8.0 Hz, $J_{2',3'}$ 10.0 Hz, H-2'), 5.055(d, 1H, $J_{gem}$ 12.5 Hz, PhCH), 5.000(bd, 1H, $J_{3',4'}$ 3.5 Hz, H-4'), 4.875[m, 2H incl. NH($J_{5'',NH}$ 10.0 Hz) and H-4''], 4.693[m, 2H incl. H-1'(d) and H-3'(dd)], 4.275[m, 2H incl. H-1($J_{1,2}$ 7.5 Hz)], 3.662(s, 3H, OCH$_3$), 3.325(dd, 1H, $J_{2,3}$ 10.0 Hz, H-2), 3.260(dd, 1H, $J_{3,4}$ 9.0 Hz H-3), 2.615(dd, 1H, $J_{3''a,4''}$ 4.5 Hz, $J_{3''a,3''e}$ 13.5 Hz, H-3''e), 2.245, 2.188, 2.085(two), 2.070 (two), 2.065, 1.988, 1.713(9s, 27H, 8 OAc, 1 NAc), 1.588(t, 1H, $J_{3''a,4''}$ 13.0 Hz H-3''a).

Anal. Calc. for $C_{56}H_{78}O_{28}N_4$: C, 53.53; H, 6.26; N, 4.46. Found: C, 53.27; H, 6.27; N, 4.50.

Trisaccharide 25: foam $[\alpha]^{22}_D$ +0.240°(c1.0 chloroform); i.r. 2113 cm$^{-1}$(N$_3$); $^1$H-nmr: 7.400(m, 5H, aromatics), 5.513 (ddd, $J_{7'',8''}$ 8.5 Hz, $J_{8'',9''a}$ 2.6 Hz, $J_{8'',9''b}$ 5.2 Hz, H-8''), 5.438(d, 1H, $J_{gem}$ 12.0 Hz, PhCH), 5.339(dd, 1H, $J_{6'',7''}$ 2.7 Hz, H-7''), 5.063[m, 3H incl. PhCH(d), NH(d, $J_{5'',NH}$ 10.5 Hz), H-2'(dd, $J_{1',2'}$ 8.0 Hz, $J_{2',3'}$ 10.0 Hz)], 4.988(bd, 1H, $J_{3',4'}$ 3.5 Hz, H-4'), 4.867(ddd, 1H, $J_{3''e,4''}$ 4.5 Hz, $J_{3''a,4''}$ 12.5 Hz, $J_{4'',5''}$ 10.5 Hz, H-4''), 4.638[m, 2H incl. H-1' (d) and H-3'(dd)], 4.238 [m, 2H, incl. H-1(d $J_{1,2}$ 8.0 Hz)], 3.662(s, 3H, OCH$_3$), 3.330(dd, 1H, $J_{2,3}$ 10.0 Hz, H-2), 2.663 (dd, 1H, $J_{3''a, 3''e}$ 12.5 Hz, H-3''e), 2.255, 2.168, 2.138, 2.075(three), 2.055, 1.988, 1.838 (7s, 27H, 8 OAc, 1 NAc), 1.663(t, 1H, H-3''a).

Anal. Calc. for $C_{56}H_{78}O_{28}N_4$: C, 53.53; H, 6.26; N, 4.46. Found: C, 53.41; H, 6.30; N, 4.73.

For identification purposes both trisaccharides 24 and 25 were acetylated (pyridine, acetic anhydride and DMAP). After the usual work up the recovered products were filtered through silica gel using ethyl acetate as eluant. The appropriate fractions were pooled and evaporated. Decoupling experiments on the $^1$H-nmr spectra confirmed the structures of both compounds.

Trisaccharide 26, $^1$H-nmr: 7.43(m, 5H, aromatics), 5.538 (ddd, $J_{7'',8''}$ 8.5 Hz, $J_{8'',9''a}$ 2.7 Hz, $J_{8'',9''b}$ 5.6 Hz, H-8''), 5.075(d, 1H, $J_{gem}$ 12.0 Hz, PhCH), 5.355 (dd, 1H, $J_{6'',7''}$ 2.5 Hz, $J_{7'',8''}$ 8.5 Hz, H-7''), 4.85–5.05 [m, 6H incl. H-4'(d, $J_{3',4'}$ 3.5 Hz), H-2' (dd, $J_{1',2'}$ 8.0 Hz, $J_{2',3'}$ 10.0 Hz), H-1'(d), H-4, H-4''(m)], 4.650(dd, 1H, H-3'), 4.280(d, 1H, $J_{1,2}$ 8.0 Hz, H-1), 3.662(s, OCH$_3$), 3.638(t, 1H, $J_{2,3}=J_{3,4}$ 9.5 Hz, H-3), 3.363(dd, 1H, H-2), 2.613(dd, 1H, $J_{3''e,4''}$ 5.0 Hz, $J_{3''e, 3''a}$ 13.0 Hz, H-3''e), 2.250, 2.180, 2.075(three), 2.050 (two), 2.030, 1.975, 1.825 (7s, 30H, 9 OAc, 1 NAc), 1.688(t, $J_{3''a,4''}$ 12.5 Hz, H-3''a).

Trisaccharide 28, $^1$H-nmr: 7.40(m, 5H aromatics), 5.450[m, 2H, incl. H-8''(m) and PhCH (d, $J_{gem}$ 12.0 Hz)], 5.368(dd, 1H, $J_{6'',7''}$ 2.5 Hz, $J_{7'',8''}$ 8.5 Hz, H-7''), 5.050(d, 1H, PhCH), 5.000(bd, 1H, $J_{3',4'}$ 3.5 Hz, H-4'), 4.80–4.98 [m, 4H incl. H-3(dd, $J_{2,3}$ 10.0 Hz, $J_{3,4}$ 9.5 Hz), H-2'(dd, $J_{1',2'}$ 8.0 Hz, $J_{2',3'}$ 10.0 Hz), NH(d) and H-4''(m)], 4.588(d, 1H, H-1'), 4.550(dd, 1H, H-3'), 4.337(d, 1H, $J_{1,2}$ 8.5 Hz, H-1), 3.750(t, 1H, $J_{4,5}$ 10.0 Hz, H-4), 3.638(s, 3H, OCH$_3$), 3.387(dd, 1H, H-2), 2.590(dd, 1H, $J_{3''e,4''}$ 5.0 Hz, $J_{3''e,3''a}$ 13.0 Hz, H-3''e), 2.207, 2.160, 2.108 (two) 2.090, 2.070, 2.055, 2.027, 1.977, 1.825, (9s, 30H, 9 OAc, 1 NAc) 1.665 (t, $J_{3''a,4''}$ 12.5 Hz, H-3''a).

8-Methoxycarbonyloctyl (5-acetamido-3,5-di-deoxy-α-D-glycero-D-galacto-2-nonulopyranosylonic acid)-(2-3)-O-(β-D-galactopyranosyl)-(1-3)-O-(2-acetamido-2-deoxy-β-D-glucopyranoside) (27)

Reduction of the azido group of compound 24 (0.100, 0.796 mmol) with hydrogen sulfide in a mixture of pyridine (3 ml), water (0.5 ml) and triethylamine (0.035 ml), followed by N-acetylation with acetic anhydride afforded the 2-acetamido-trisaccharide (76%). Hydrogenation of this compound (0.136 g, 0.104 mmol) in the presence of palladium on carbon and subsequent de-O-acetylation gave the title trisaccharide 27 (0.070 g, 79.5%), $[\alpha]^{22}_D$ −19.8° (c1.0, water); $^1$H-nmr(D$_2$O): 4.555(d, 1H, J 8.2 Hz) and 4.490 (d, 1H, J 8.0 Hz): H-1 and H-1', 4.083 (dd, 1H, $J_{2',3'}$ 10.0 Hz, $J_{3',4'}$ 3.2 Hz, H-3'), 3.683 (s, OCH$_3$), 2.763 (dd, 1H, $J_{3''e,4''}$ 4.6 Hz, $J_{3''e,3''a}$ 12.1 Hz, H-3''e), 2.388 (t, 2H, J 6.5 Hz, CH$_2$CO), 2.025, 2.015 (2s, 6H, 2 NAc), 1.788 (t, 1H, $J_{3''a,4''}$ 12.0 Hz, H-3''a), 1.61[m, 4H, (CH$_2$)$_2$], 1.363 [m, 8H, (CH$_2$)$_4$].

8-Methoxycarbonyloctyl (benzyl 5-acetamido-4,7,8,9-tetra-O-acetyl-3,5-di-deoxy-α-D-glycero-D-galacto-2-nonulopyranosylonate)-(2-3)-O-(2,4,6-tri-O-acetyl-β-D-galactopyranosyl)-(1-4)-O-(2-acetamido-6-O-acetyl-2-deoxy-β-D-glucopyranoside) (29)

The azido group of compound 25 (0.410 g, 0.327 mmol) was reduced as indicated above for the preparation of compound 27. Chromatography provided compound 29 (0.326 g, 78.5%) as a syrup: $[\alpha]^{22}_D$ +21.2° (c1.0, chloroform); $^1$H-nmr: 7.40 (m, 5H, aromatics), 5.575(d, 1H, $J_{2,NH}$8.0 Hz, NH-2), 5.475(ddd, 1H, $J_{7'',8''}$ 8.5 Hz, $J_{8'',9''a}$ 5.6 Hz, $J_{8'',9''b}$ 2.6 Hz, H-8''), 5.440(d, 1H, $J_{gem}$ 12.5 Hz, PhCH), 5.350 (dd, 1H, $J_{6'',7''}$ 2.6 Hz, H-7''), 5.050[m, 2H, incl. H-2'(dd, $J_{1',2'}$ 8.0 Hz, $J_{2',3'}$ 10.0 Hz and PhCH (d)], 5.000(bd, 1H, $J_{3',4'}$3.5 Hz, H-4'), 4.875[m, 2H, incl. NH-5'' (d, $J_{5'',NH}$ 10.0 Hz) and H-4''(m)], 4.775(d, 1H, $J_{1,2}$ 8.0 Hz, H-1), 4.650[m, 2H, incl. H-1'(d) and H-3'(dd)], 3.675(s, 3H, OCH$_3$), 3.500[m, 3H, incl. H-6''(dd, $J_{5'',6''}$ 10.5 Hz) and H-2(m)], 2.600(dd, 1H, $J_{3''a,4''}$ 4.0 Hz, $J_{3''a,3''e}$ 13.0 Hz, H-3''e), 2.262, 2.168, 2.082, 2.075 (three), 2.050, 1.980 (two), 1.825 (7s, 30H, 8 OAc, 2 NAc).

Anal. Calc. for C$_{58}$H$_{82}$O$_{29}$N$_2$: C, 54.80; H, 6.50; N, 2.20. Found: C, 54.51; H, 6.54; N, 2.50.

The i.r. spectrum showed the absence of the azide absorption.

8-Methoxycarbonyloctyl (5-acetamido-3,5-di-deoxy-α-D-glycero-D-galacto-2-nonulopyranosylonic acid)-(2-3)-O-(β-D-galactopyranosyl)-(1-4)-O-(2-acetamido-2-deoxy-β-D-glucopyranoside) (30)

The trisaccharide 29 was deprotected and purified as indicated previously for the preparation of compound 27 to provide for compound 30 (79%): $[\alpha]^{22}_D$−8.3° (c1.0, water); $^1$H-nmr(D$_2$O): 4.550 (d, 1H, J 8.0 Hz) and 4.513 (d, 1H, J 7.2 Hz): H-1 and H-1', 4.115 (dd, 1H, $J_{2',3'}$ 10.0 Hz, $J_{3',4'}$3.0 Hz, H-3'), 3.955(dd, 1H, H-4'), 3.685(s, OCH$_3$), 2.755(dd, 1H, $J_{3''e,3''a}$12.5 Hz, $J_{3''e,4''}$ 4.6 Hz, H-3''e), 2.388 (t, 2H, J 6.5 Hz, CH$_2$CO), 2.025(s, 6H, 2 NAc), 1.800 (t, 1H, $J_{3''a,4''}$ 12.5 Hz, H-3''a), 1.600 [m, 4H, (CH$_2$)$_2$], 1.325[m, 8H, (CH$_2$)$_4$].

EXAMPLE VIII

Preparation of 8-methoxycarbonyloctyl (benzyl 5-acetamido-4,7,8,9,-tetra-O-acetyl-3,5-dideoxy-α-D-glycero-D-galacto-2-nonulopyranosylonate)-(2-3)-O-(4,6-di-O-acetyl-2-O-benzoyl-β-D-galactopyranosyl)-(1-4)-O-(2-azido-2-deoxy-β-D-glucopyranoside) (32) and of 8-methoxycarbonyloctyl (benzyl 5-acetamido-4,7,8,9-tetra-O-acetyl-3,5-dideoxy-α-D-glycero-D-galacto-2-nonulopyranosylonate)-(2-3)-O-(4,-di-O-acetyl-2-O-benzoyl-glucopyranosyl)-(1-3)-O-(2-azido-2-deoxy-β-D-glucopyranoside) (33)

Trimethysilyltrifluoromethane sulfonate (0.159 g, 0.715 mmol) in dichloromethane (1.5 mL) was syringed in three portions (every hour) into the a flask containing 16 (0.335 g, 0.355 mmol), calcium sulfate (0.500 g, crushed), the diol 31 (0.435 g, 0.710 mmol prepared from the azido glucoside used in Example VII by selective silylation) in dichloromethane (3 mL). After 4 hours at 22° C., the reaction was stopped by addition of triethylamine (0.071 mL). Dilution with dichloromethane, filtration and successive washing with aqueous sodium bicarbonate and water gave the crude product after drying and evaporation. Chromatography on silica gel (36 g) using a mixture of hexane:ethyl acetate:ethanol (10:10:1) gave a mixture (2:1) of the two trisaccharides with 1-4 and 1-3 linkages, respectively (0.432 g, 81%).

Tetraethylammonium chloride (0.392 g, 2.63 mmol), potassium fluoride (0.153 g, 2.63 mmol) and benzoic acid (0.053 g, 0.434 mmol) were added to the above mixture (0.0590 g, 0.394 mmol) in acetonitrile (15 mL). After stirring overnight at 22° C., the solvent was evaporated in vacuo, the residue diluted with dichloromethane and washed with water. Drying and evaporation left the crude mixture (0.574 g) which was chromatographed on silica gel (37 g) using a mixture of chloroform and acetone (70:30). Collection and evaporation of the appropriate fractions gave 32 (0.360 g, 60%): i.r. 2113 cm$^{-1}$(N$_3$); $^1$H-nmr: 5.78(m, 1H, H-8''), 5.46(d, 1H, $J_{gem}$ 12.0, PhCH), 5.33 (dd, 1H, $J_{1',2'}$ 8.0 Hz, $J_{2',3'}$ 10.0 Hz, H-2'), 4.18(d, 1H, $J_{1,2}$ 8.0 Hz, H-1), 3.68(s, 3H, OCH$_3$), 3.30(dd, 1H, $J_{1,2}$ 8.0 Hz, $J_{2,3}$ 10.0 Hz H-2), 2.56(dd, $J_{3''e,4''}$ 4.5 Hz, $J_{3''e,3''a}$ 13.0 Hz, H-3''e), 2.28(t, 2H, J 7.5 Hz, CH$_2$CO$_2$), 2.22, 2.14, 2.12, 2.08, 1.94, 1.76, 1.52, (7s, 21H, 6 OAc, 1 NAc), 1.68, (t, $J_{3''a,4''}$ 13.0 Hz, H-3''a) and compound 33 (0.180 g, 29%): i.r. 2113 cm$^{-1}$(N$_3$); $^1$H-nmr: 5.60 (m, 1H, H-8''), 5.44(d,1H, $J_{gem}$ 12.0, PhCH), 5.47(dd, 1H, $J_{1',2'}$ 8.0 Hz, $J_{2',3'}$ 10.0 Hz, H-2'), 5.20(dd, 1H, $J_{6'',7''}$ 2.5 Hz, $J_{7'',8''}$ 10.0 Hz, H-7''), 4.28(d, 1H, $J_{1,2}$ 8.0 Hz, H-1), 3.67(s, 3H, OCH$_3$), 2.68(dd, 1H, $J_{3''e,4''}$ 4.5 Hz, $J_{3''e,4''}$ 13.0 Hz, H-3''e), 2.28 (t, 2H, J 7.5 Hz, CH$_2$—CO), 2.22, 2.12, 2.09, (two), 1.96, 1.78, 1.58, (6s, 21H, 6 OAc, 1 NAc), 1.83(t, 1H, $J_{3''a,4''}$ 13.0 Hz, H-3''a).

For identification purposes, both trisaccharides 32 and 33 were peracetylated with acetic anhydride, pyridine and dimethylaminopyridine. Peracetylated 32; $^1$H-nmr: 4.89(dd, 1H, $J_{2,3}$ 10.5 Hz, $J_{3,4}$ 9.7 Hz, H-3), 4.23(d, $J_{1,2}$ 8.0 Hz, H-1), 3.78(t, $J_{4,5}$ 10.0 Hz, H-4), 2.37 (dd, H-2). Peracetylated 33, $^1$H-nmr: 4.80(m, 4H, incl. H-4), 4.20 (d, $J_{1,2}$ 8.0 Hz, H-1), 3.67[m, 4H incl. OCH$_3$(s) and H-3], 3.20 (dd, $J_{2,3}$ 10.0 Hz, H-2).

In both spectra the signals, which are overlapping with others, have been identified by decoupling experiments.

Preparation of 8-methoxycarbonyloctyl (5-acetamido-3,5-di-deoxy-α-D-glycero-D-galacto-2-nonulopyranosylonic acid)-(2-3)-O-(β-D-galactopyranosyl)-(1-4)-(2-acetamido-2-deoxy-β-D-glucopyranoside) (30)

Hydrogen sulfide was bubbled through a solution of the trisaccharide 32 (0.070 g, 0.055 mmol), triethylamine (0.050 mL, water (0.500 mL) and pyridine (2.00 mL). After 20 hours at 22° C., acetic anhydride (0.250 mL) was syringed into the cooled mixture which was then co-evaporated with an excess of toluene. Chromatography of the residue on silica gel (7 g) using a mixture of toluene:ethanol (10:1) gave the pure intermediate (0.049 g, 68%).

$^1$H-nmr: 5.66(m, 1H, H-8''), 5.37 (d, 1H, $J_{gem}$ 12.0 Hz, PhCH), 5.25 (dd 1H, $J_{1',2'}$ 8.0 Hz, $J_{2',3'}$ 10.0 Hz, H-2'), 3.59 [m, incl. OCH$_3$(s)], 2.47(dd, 1H, $J_{3''e,3''a}$ 13.5 Hz, $J_{3''e,4''}$ 4.5 Hz, H-3''e), 2.14, 2.04, 2.03, 2.02, 1.92, 1.86, 1.68, 1.43, (8s, 24H, 6 OAc, 2 NAc).

i.r. showed the absence of azide absorption.

The above intermediate (0.049 g, 0.0375 mmol) was reduced at atmosphere pressure in methanol (2 mL) in the presence of Pd/C (5%, 0.050 g) for 2 hours. Removal of the catalyst and evaporation left a residue (0.042 g) which was treated with a 0.2N solution of sodium methoxide in methanol for 3 days at 22° C. Deionization with resin (IRC 50, H+ form), filtration and evaporation left a residue (0.034 g) which was chromatographed on Iatrobeads (6RS 8060,1.5 g) using a mixture of chloroform, methanol and water (65:35:8) as eluant giving 30 (0.037 g, 75%): $[\alpha]^{22}_D$ −8.3°(c1.O, water); $^1$H-nmr: 4.55 (d, 1H, J 8.0 Hz) and 4.51 (d, 1H, J 7.2 Hz): H-1 and H-1', 4.11 (dd, 1H, $J_{2',3'}$ 10.0 Hz, $J_{3',4'}$ 3.0 Hz, H-3'), 3.68 (s, OCH$_3$), 2.75(dd, 1H, $J_{3''e,4''}$ 4.5 Hz, $J_{3''e,3''a}$ 12.5 Hz, H-3''e), 2.38 (t, 2H, J 6.5 Hz, CH$_2$CO), 2.025 (s, 6H, 2 NAc), 1.80(t, 1H, $J_{3''a,4''}$ 12.5 Hz, H-3''a), 1.60 (m, 4H) and 1.32 (m, 8H): methylenes.

EXAMPLE IX

Preparation of Compound 35: The 19-9 Tetrasaccharide

8-Methoxycarbonyloctyl (5-acetamido-3,5-di-deoxy-α-D-glycero-D-galacto-2-nonulopyranosylonic acid)-(2-3)-O-β-D-galactopyranosyl-(1-3)-O-[α-L-fucopyranolsyl-(1-4)-O-]-2-acetamido-2-deoxy-β-D-glucopyranoside) (35)

Tri-O-benzyl fucopyranosyl bromide freshly prepared from tri-O-benzyl fucopyranose (1.78 g, 4.11 mmol) in dichloromethane (2 ml) was added to the starting material 24 (0.840 g, 0.68 mmol), molecular sieves 4A (1.0 g, crushed), dry tetraethylammonium bromide (0.144 g, 0.686 mmol) and dimethylformamide (0.50 ml) in dichloromethane (2.0 ml). The mixture was stirred at 22° C. TLC (chloroform:acetone 70:30 and hexane:ethyl acetate:ethanol 10:10:1) indicated a complete reaction in about 30 hours. Some methanol was added and stirring was continued for a few hours. The content of the flask was diluted with dichloromethane, filtered on paper, washed with a solution of sodium bicarbonate, water and brine. The crude product obtained was chromatographed on silica gel (90 g) using a mixture of hexane:ethyl acetate:ethanol (70:30:1) as eluant, to give compound 34 (0.978 g, 86%) as a syrup: $[\alpha]^{22}_D$ +0.125° (c1.O chloroform); i.r. 2116 cm$^{-1}$ (N$_3$); $^1$H-nmr: 7.30(m, 20H, aromatics), 5.500(m, 1H, $J_{7''',8'''}$ 8.6 Hz, $J_{8''',9'''a}$ 2.8 Hz, $J_{8''',9'''b}$ 4.2 Hz, H-8'''), 5.450(d, 1H, $J_{gem}$ 12.0 Hz, PhCH), 5.387(dd, 1H, $J_{6''',7'''}$ 2.8 Hz, H-7'''), 5.325(d, 1H, $J_{1',2'}$ 8.0 Hz, H-1'), 5.313 (d, 1H, PhCH), 5.287(bd, 1H, $J_{3',4'}$ 3.5 Hz, H-4'), 4.967(dd, 1H, $J_{2',3'}$ 10.0 Hz, H-2'), 4.674(dd, 1H, H-3'), 4.300(dd, 1H, $J_{9'''a,9'''b}$ 12.5 Hz, H-9'''a), 4.217(d, 1H, $J_{1,2}$ 8.0 Hz, H-1), 3.750(t, 1H, $J_{3,4}=J_{4,5}$ 9.5 Hz, H-4), 3.655(s, 3H, OCH$_3$), 3.612(t, 1H, $J_{2,3}$ 9.5 Hz, H-3), 3.495(dd, $J_{5''',6'''}$ 11.0 Hz, H-6'''), 3.250(dd, H-2), 2.587(dd, 1H, $J_{3'''e,4'''}$ 4.5 Hz, $J_{3'''a,3'''e}$ 13.5 Hz, H-3'''e), 2.250, 2.195, 2.060(two), 2.040, 2.030, 1.980, 1.825, 1.755(27H, 8 OAc, 1 NAc) 1.662(t, $J_{3'''a,4'''}$ 13.5 Hz, H-3'''a), 1.237(d, $J_{5'',6''}$ 7.5 Hz, H-6'').

Anal. Calc. for C$_{83}$H$_{106}$O$_{32}$N$_4$: C,59.6; H, 6.39; N, 3.35. Found: C, 59.36; H, 6.40; N, 3.22.

Hydrogen sulfide was slowly bubbled into a solution of the starting material 34 (0.600 g, 0.359 mmol) in a mixture of pyridine (39 ml), water (5.8 ml) and triethylamine (1.45 ml) while cooling in ice for 2 hours and at room temperature for about 5 hours. After overnight at 22° C., TLC (toluene:ethanol 10:1 or chloroform:acetone 85:15) indicated the completion of the reaction at which time acetic anhydride (4.5 ml) was added.

From similar glycosylation reactions compound 34 (0.860 g, 0.514 mmol) was obtained and treated as above. The crude material was co-evaporated with an excess of toluene. The residue was then applied on a column of silica gel (70 g) and eluted with toluene (300 ml) and a mixture of toluene and ethanol (100:1, 600 ml) removed all colored material. Elution with the same solvents (100:7) gave some minor fractions followed by the main product with the 2-acetamido group (0.750 g, 86%) as a syrup: $[\alpha]^{22}_D$ −12.9°(c1.0 chloroform); $^1$H-nmr: 7.40(m, 20H, aromatics) 6,220(bd, 1H, $J_{2,NH}$ 10.0 Hz, NH-2), 5.425[m, 2H incl. PhCH(d, $J_{gem}$ 12.0 Hz) and H-8''' (m)], 5.350(dd, 1H, $J_{6''',7'''}$ 2.5 Hz, $J_{7''',8'''}$ 9.0 Hz, H-7'''), 5.075[m, 2H incl. PhCH (d), and H-4'(bd, $J_{3',4'}$ 3.5 Hz)], 4.675-5.025[m, incl. H-2'(dd, $J_{1',2'}$ 8.0 Hz, $J_{2',3'}$ 10.0 Hz)], 4.563 (dd, H-3'), 3.65(s, 3H, OCH$_3$), 3.450(dd, 1H, $J_{5''',6'''}$ 11.5 Hz, H-6'''), 2.575(dd, 1H, $J_{3'''e,3'''a}$ 13.0 Hz, $J_{3'''e,4'''}$ 4.5 Hz, H-3'''e), 2.205, 2.168, 2.072, 2.050(three), 1.975, 1.850, 1.830, 1.813(30H, 8 OAc, 2 NAc), 1.60[m, 5H, incl. H-3'''a and (CH$_2$)$_2$], 1.200(d, $J_{5'',6''}$ 7.5 Hz, H-6'').

Irradiation of NH(d) at 6.22 indicates that H-2 is at 3.80.

The i.r. spectrum indicated the absence of azide absorption.

Anal. Calc. for C$_{85}$H$_{110}$O$_{33}$N$_2$: C, 60.48; H, 6.57; N, 1.70. Found: C,60.36; H, 6.46; N, 1.70.

This intermediate tetrasaccharide (0.715 g, 0.436 mmol) was hydrogenated at atmospheric pressure in methanol (60 ml) in the presence of catalyst(5% Pd/C, 0.700 g, pre-hydrogenated in the same solvent and decanted). TLC developed with chloroform:methanol:water (65:35:3) indicated a rapid reaction. After 4 hours, the catalyst was filtered on paper and washed several times with methanol. The solvent was evaporated in vacuo. This product was dissolved in a 0.2N sodium methoxide in methanol (20 ml) and stirred at 22° C. for 3 days. TLC developed with chloroform: methanol:water (65:35:8) was used to monitor the reaction. After complete reaction, the solution was cooled to −10° C. and some resin (IRC 50, H+ form, methanol washed, 6 g) was added portion-wise until neutral pH. Evaporation and freeze drying left a slightly yellowish powder (0.435 g, quantitative) which was further run through Iatrobeads (6 RS 8060) using a mixture of chloroform:water:methanol: (65:35:6) to give pure compound 35

$[\alpha]^{22}_D$ −49.4°(c1.0, chloroform); $^1$H-nmr(D$_2$O): 5.005(d, 1H, J$_{1',2'}$4.0 Hz, H-1'), 4.866(q, 1H, J$_{5'',6''}$ 6.8 Hz, H-5''), 4.525 (d, 2H, J$_{1,2}$=J$_{1',2'}$=7.8 Hz, H-1 and H-1'), 4.056 (m, 2H, incl. H-3'), 3.691(s, OCH$_3$), 2.767(dd, 1H, J$_{3'''a,4'''}$ 4.6 Hz, J$_{3'''a,3'''e}$ 12.8 Hz, H-3'''e), 2.392 (t,2H, J 6.5 Hz, CH$_2$—CO), 1.925, 1.979(2s, 6H, 2 NAc), 1.765 (t, 1H, J$_{3'''a,4'''}$ 12.6 Hz, H-3'''a), 1.584 [m, 4H, (CH$_2$)$_2$], 1.296 [m, 8H, (CH$_2$)$_4$], 1.170 (d, 3H, H-6'').

EXAMPLE X

Synthesis of Compound 37: Sialo-X Tetrasaccharide

8-Methoxycarbonyloctyl
(5-acetamido-3,5-di-deoxy-α-D-glycero-D-galacto-2-nonulopyranosylonic
acid)-(2-3)-O-β-D-galactopyranosyl-(1-4)-O-[α-L-fucopyranosyl-(1-3)-O-]-2-acetamido-2-deoxy-β-D-glucopyranoside (37)

The starting material 29 (0.139 g, 0.109, mmol) was reacted with tri-O-benzyl fucopyranosyl bromide as indicated previously for the preparation of 34. TLC (chloroform:acetone 70:30 and toluene:ethanol 100:10) indicated the completion of the reaction in less than 24 hours. Work-up as indicated before and purification of the reaction product by chromatography on silica gel (8 g) using a mixture of chloroform:acetone (75:25) gave 36 (0,143 g, 77%) as a syrup: $[\alpha]^{22}_D$− 12.0° (c1.0, chloroform); $^1$H-nmr: 7.35(m, 25H aromatics), 5.870 (d, 1H, J$_{2,NH}$ 8.0 Hz, NH-2), 4.975(m, 1H, H-8'''), 4.925(d, 1H, J$_{gem}$ 12.5 Hz, PhCH), 5.375(dd, 1H, J$_{6''',7'''}$ 2.7 Hz, J$_{7''',8'''}$ 9.0 Hz, H-7'''), 4.413 (q, 1H, J$_{5',6'}$7.0 Hz, H-5'), 3.67 (s, OCH$_3$), 3.487[m, 2H, incl. H-6''' (dd, J$_{5''',6'''}$ 10.0 Hz)], 2.587 (dd, 1H, J$_{3'''e,4'''}$ 4.5 Hz, J$_{3'''a,3'''e}$ 13.0 Hz, H-3'''e), 2.200, 2,163, 2.063 (two), 2.038 (two), 1.975, 1.875, 1.825, 1.750 (8s, 30H, 8 OAc, 2 NAc), 1.18(d, 3H, H-6').

The tetrasaccharide 36 (0.274 g, 0.166 mmol) was de-O-protected as previously indicated for the preparation of 35. The crude material recovered after de-O-acetylation (0.140 g) was chromatographed on Iatrobeads (3 g) using a mixture of chloroform:methanol:water (65:35:5) which provided compound 37 (0.118 g, 74%): $[\alpha]^{22}_D$−41.0° (c1.0, water); $^1$H-nmr(D$_2$O): 5.100 (d, 1H, J$_{1',2'}$ 3.8 Hz, H-1'), 4.825 (q, 1H, J$_{5',6'}$ 6.5 Hz, H-5'), 4.520 (d, 2H, J$_{1,2}$=J$_{1'',2''}$ 8.0 Hz, H-1 and H-1''), 4.085 (dd, 1H J$_{3'',4''}$ 4.0 Hz, J$_{2'',3''}$ 9.8 Hz, H-3') 3.668(s, OCH$_3$), 2.763 (dd, 1H, J$_{3'''e,4'''}$ 4.6 Hz, J$_{3'''e,3'''a}$ 12.4 Hz, H-3'''e), 2.388 (t, 2H, J 7.5 Hz, CH$_2$CO), 2.030, 2.018 (2s, 6H, 2 NAc), 1.795 (t, 1H, J$_{3'''a,4'''}$ 12.2 Hz, 4-3'''a), 1.587 [m, 4H, (CH$_2$)$_2$], 1.295 [m, 8H, (CH$_2$)$_4$], 1.165 (d, 3H, H-6').

EXAMPLE XI

Preparation Synthetic Antigens from Tetrasaccharides 35 and 37

The tetrasaccharide 35 (0.021 g) was treated with 95% hydrazine hydrate for 1 hour to effect the conversion of the methyl ester to the hydrazide derivative compound 38. This product was co-evaporated with n-butanol:water 1:1 several times to effect the removal of residual hydrazine and reacted as follows to give the synthetic antigen.

Compound 38 (0.020 g, 0.020 mmol) was dissolved in dimethylformamide (0.5 ml) and cooled to −20° C. A solution of dioxane (0.020 ml) that was 4.0M in hydrochloric acid was added followed by t-butyl nitrite (0.005 ml) and the resulting mixture stirred for 30 minutes. At that time sulfamic acid (0.001 g, 0.010 mmol) was added and stirred for 15 minutes. This solution was added to a solution of bovine serum albumin (BSA) (0.025 g) in N-ethyldiethanolamine buffer (0.2M, adjusted to pH 9 with hydrochloric acid) at 0° C. After standing for 18 hours, the solution was dialyzed against water for five exchanges with a 10,000 molecular weight cut-off. Lyophilization of the contents of the dialysis cell gave the 19-9 synthetic glycoconjugate 43 (0.028 g). Analysis for hexoses by phenol-sulfuric assay indicated the presence of 20 moles of hapten per mole of BSA. Analysis for N-acetyl neuraminic acid corroborated this result.

Conversion of the ester 37 to its corresponding hydrazide 39 and reaction of this as described above gave the sialyl-X synthetic glycoconjugate. Similar synthetic glycoconjugates have been prepared with alternate carrier molecules such as human serum albumin, keyhole limpet hemocyanin and horse radish peroxidase through the reaction of compound 38 and 39 as described above.

These products can be used to study the binding properties of antibodies, bacterial and viral receptors and other biomolecules.

EXAMPLE XII

Preparation of Synthetic Immunoadsorbents from Compounds 38 and 39

The hydrazide 38 or 39 (0.020 g) was converted to the reactive acyl azide as described above in example XI and reacted with silylaminated crystobilite (20 g) suspended in dry acetonitrile (60 ml) for 18 hours at which time the solid was filtered and washed with water and then methanol. This was then dried at 70° C. to give the synthetic immunoadsorbent having the reactivity conferred by structure 38 or 39. Phenol-sulfuric and sialic acid assays showed an incorporation of 0.7–0.8 micromoles of hapten per gram of support. Many other aminated supports have been used to prepare such immunoadsorbents such as controlled pore glass, aminated polysaccharides and aminated polymers. These products can be used to isolate, purify or remove antibodies, lectins and other biomolecules which have reactivity or specificity for the structures of compounds 38 or 39.

EXAMPLE XIII

Detection of 19-9 Reactive Antibodies with the Synthetic Glycoconjugate Prepared from Compound 38

The wells of plastic plates were coated with the 19-9 synthetic glycoconjugate formed from compound 38 in the following manner. A solution of the conjugate (50 μg/ml) in buffer (50 mM NaH$_2$PO$_4$/Na$_2$HPO$_4$, 5 mM MgCL$_2$, 15 mM NaN$_3$, pH 7.5) (100 μl) was dispensed into each well and incubated for 18 hours at ambient temperature at which time the coating solution was removed by aspiration. A phosphate buffered saline (PBS) solution 5% in BSA (200 μl) was then dispensed into the wells and incubated for 4 hours at ambient temperature at which time this was removed by aspiration. The wells were washed successively with 2 times 200 μl of PBS and 200 μl of distilled water.

A working solution of antibody was prepared for reaction with the coated wells in the following manner. With ascites stock, dilution of the antibody with 1% BSA in PBS between 1/50 to 1/100 was done. With cell supernatant containing antibodies, neat to 1/5 dilutions was used for reaction and with purified antibodies at concentrations in the range of 1 mg/ml, dilutions of 1/100 to 1/200 was used. These are only suggested dilution ranges and these may be altered to suit the purpose of the assay and the nature of the antibody avidities and affinities.

A solution of antibody (100 μl) was dispensed into wells coated with the synthetic glycoconjugate formed from compound 38 and control wells coated with other synthetic glycoconjugates, for example, the Lewis$^a$ antigen 40, the 2-6 analogue of 38, antigen 41 and the linear 2-3 antigen 42. The antibody solution was incubated for 1 to 4 hours and then removed and the wells were washed with 200 μl of PBS three times. Alkaline phosphatase labelled anti-immunoglobulin in 1% PBS (100 μl) was then dispensed into the wells and incubated for 1-3 hours at which time the wells were aspirated and washed 3 times with PBS. A solution of phosphatase substrate (100 μl) was then added to the wells and incubated to allow colour development. The wells were read at $A_{405}$ at intervals to give the data of reactivity of the antibody with the various synthetic glycoconjugates as shown below.

| Reaction of Anti-19-9 Antibody with Synthetic Antigens | | | | | |
|---|---|---|---|---|---|
| Wells Coated With | 40 | 41 | 42 | 43 | BSA |
| Absorbance $A_{405}$ | 0.232 | 0.148 | 0.185 | 0.640 | 0.201 |

The above results clearly show specific reaction of this antibody with the synthetic glycoconjugate 43 formed from the synthetic structure 35. The related conjugates show the same reactivity as the control wells which were coated with the BSA carrier molecule. Competitive inhibition ELISA assays were also conducted wherein the free synthetic glycoconjugates were added as inhibitors. Only 43 gave any significant inhibition and this reduced the absorbance to background values. This shows that this assay format with the synthetic antigen coated on wells will function not only as a method for the detection of anti-19-9 antibodies but also for the detection of the 19-9 structure itself in fluids.

We claim:

1. A compound of the formula:

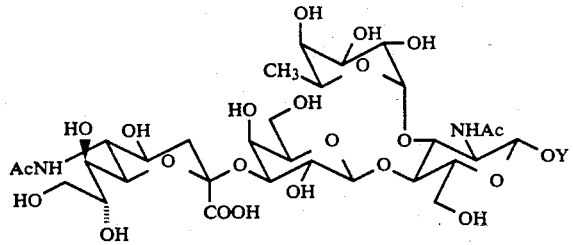

or

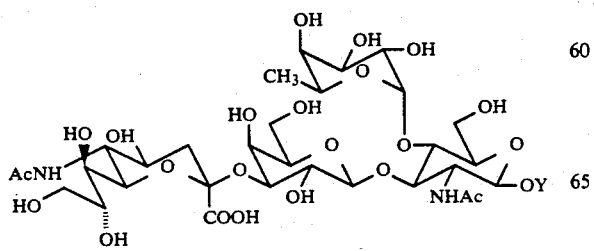

wherein Ac is an acyl group of from 1 to 6 carbon atoms, and Y is selected from the group consisting of hydrogen, lower alkyl of from 1 to 6 carbon atoms, a linking arm and a moiety comprising a chromatographic support.

2. The compound of claim 1 wherein Y is a linking arm.

3. The compound of claim 2 wherein the linking arm has the formula:

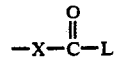

wherein X is a straight or branched chain saturated or unsaturated hydrocarbylene of 3-19C wherein 1-3 nonadjacent $CH_2$ may optionally be replaced by NR, S, or O wherein R is H or alkyl (C1-6), and L is a leaving group or is convertible to a leaving group.

4. The compound of claim 1 wherein Y comprises a chromatographic support covalently attached to said compound.

5. The support of claim 4 wherein the covalent attachment is made through a linking arm.

6. The support of claim 5 wherein the covalent attachment through the linking arm to the chromatographic support is made by reacting the compound having a linking arm of the formula:

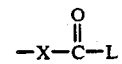

with the chromatographic support so as to form a covalent attachment
wherein X is a straight or branched chain saturated or unsaturated hydrocarbylene of from 3 to 19 carbon atoms wherein 1 to 3 nonadjacent $CH_2$ units may optionally be replaced by NR, S, or O, wherein R is H or alkyl of from 1 to 6 carbon atoms, and L is a leaving group or a group convertible to a leaving group.

7. A compound of the formula:

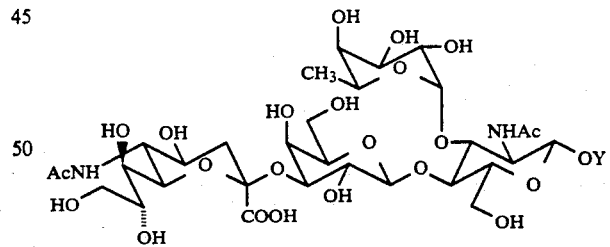

or

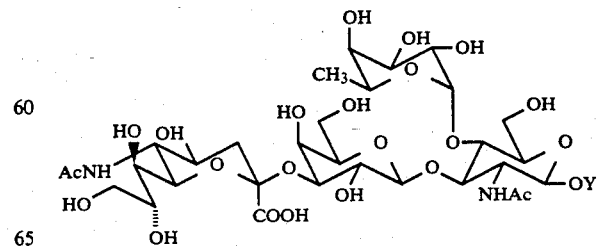

wherein Ac is an acyl group of from 1 to 6 carbon atoms, and Y is selected from the group consisting of hydrogen, lower alkyl of from 1 to 6 carbon atoms, and a linking arm of the formula:

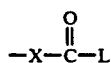

wherein X is a straight or branched chain saturated or unsaturated hydrocarbylene of from 3 to 19 carbon atoms wherein 1 to 3 nonadjacent $CH_2$ units may optionally be replaced by NR, S, or O, wherein R is H or alkyl of from 1 to 6 carbon atoms, and L is a leaving group or a group convertible to a leaving group or sodium salts thereof.

8. A compound of claim 7 wherein Y is selected from the group consisting of alkyl of from 1 to 6 carbon atoms and a linking arm of the formula

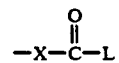

wherein X is a straight or branched saturated or unsaturated hydrocarbylene of from 3 to 19 carbon atoms wherein 1 to 3 nonadjacent $CH_2$ units may optionally be replaced by NR, S, or O wherein R is hydrogen or alkyl of from 1 to 6 carbon atoms, and L is a leaving group or a group convertible to a leaving group.

* * * * *